United States Patent
Aragaki

(10) Patent No.: US 10,849,598 B2
(45) Date of Patent: Dec. 1, 2020

(54) ULTRASONIC MEASUREMENT APPARATUS, ULTRASONIC IMAGING APPARATUS, AND ULTRASONIC MEASUREMENT METHOD

(71) Applicant: Seiko Epson Corporation, Tokyo (JP)

(72) Inventor: Takumi Aragaki, Matsumoto (JP)

(73) Assignee: Seiko Epson Corporation

( * ) Notice: Subject to any disclaimer, the term of this patent is extended or adjusted under 35 U.S.C. 154(b) by 1309 days.

(21) Appl. No.: 14/928,076

(22) Filed: Oct. 30, 2015

(65) Prior Publication Data

US 2016/0120513 A1 May 5, 2016

(30) Foreign Application Priority Data

Oct. 31, 2014 (JP) .................................. 2014-222474

(51) Int. Cl.
*A61B 8/08* (2006.01)
*G01S 15/89* (2006.01)
(Continued)

(52) U.S. Cl.
CPC .......... *A61B 8/5207* (2013.01); *A61B 8/5269* (2013.01); *G01S 7/52038* (2013.01);
(Continued)

(58) Field of Classification Search
CPC ..... A61B 8/5207; A61B 8/5215; A61B 8/461; A61B 88/5269; G01S 15/8977; G01S 7/52038; G01S 15/8963
See application file for complete search history.

(56) References Cited

U.S. PATENT DOCUMENTS

| 2007/0165488 | A1* | 7/2007 | Wildey | G01F 23/284 367/101 |
| 2010/0036255 | A1* | 2/2010 | Itani | G01S 7/52038 600/458 |
| 2010/0142781 | A1* | 6/2010 | Walker | G01S 7/5205 382/131 |

FOREIGN PATENT DOCUMENTS

| JP | 2002-360569 A | 12/2002 |
| JP | 2011-010793 A | 1/2011 |

OTHER PUBLICATIONS

Lagg 2010 IMPRS course, 66 pages; internet acessibility: https://www2.mps.mpg.de/homes/lagg/talks/2004_IMPRS_spectral_analysis/span.pdf (Year: 2010).*

(Continued)

*Primary Examiner* — Keith M Raymond
*Assistant Examiner* — Patrick M Mehl
(74) *Attorney, Agent, or Firm* — Harness, Dickey & Pierce, P.L.C.

(57) ABSTRACT

An ultrasonic measurement apparatus includes a transmission processing unit that performs processing for transmitting an ultrasonic wave with respect to a target object, a reception processing unit that performs reception processing of an ultrasonic echo with respect to the transmitted ultrasonic wave, and a processing unit that performs processing with respect to a reception signal from the reception processing unit. The processing unit performs coupling coefficient specification processing of a plurality of first basis waves which configure the reception signal, with respect to the reception signal corresponding to a transmission pulse signal which is transmitted by the transmission processing unit. The processing unit performs conversion processing for converting the reception signal into a reconfiguration signal based on a plurality of coupling coefficients which are specified through the coupling coefficient specification pro- (Continued)

cessing, and a second basis wave having a number of wave cycles less than that of the first basis wave.

20 Claims, 17 Drawing Sheets

(51) Int. Cl.
*G01S 7/52* (2006.01)
*A61B 8/00* (2006.01)
(52) U.S. Cl.
CPC ...... *G01S 15/8963* (2013.01); *G01S 15/8977* (2013.01); *A61B 8/4405* (2013.01); *A61B 8/4427* (2013.01); *A61B 8/461* (2013.01); *A61B 8/5215* (2013.01)

(56) References Cited

OTHER PUBLICATIONS

Hedrick 2008 JDMS 24:11-15 (Year: 2008).*
Morin et al. 2013 IEEE International Conference on Image Processing—ICIP 2013, Sep. 2013, Melbourne, Australia. pp. 1413-1417 (Year: 2013).*
Tur et al. 2011 arXiv:1003.282v4 Jan. 5, 2011, 42 pages (Year: 2011).*
Kohn 2006 Encyclopedia of Biomedical Engineering Ed. Metin Akay Wiley and Sons p. 260-283 (Year: 2006).*
Rasmussen et al., "Third Harmonic Imaging using Pulse Inversion", Paper presented at the IEEE International Ultrasonics Symposium, Orlando Florida, 2011 (5 pages).

\* cited by examiner

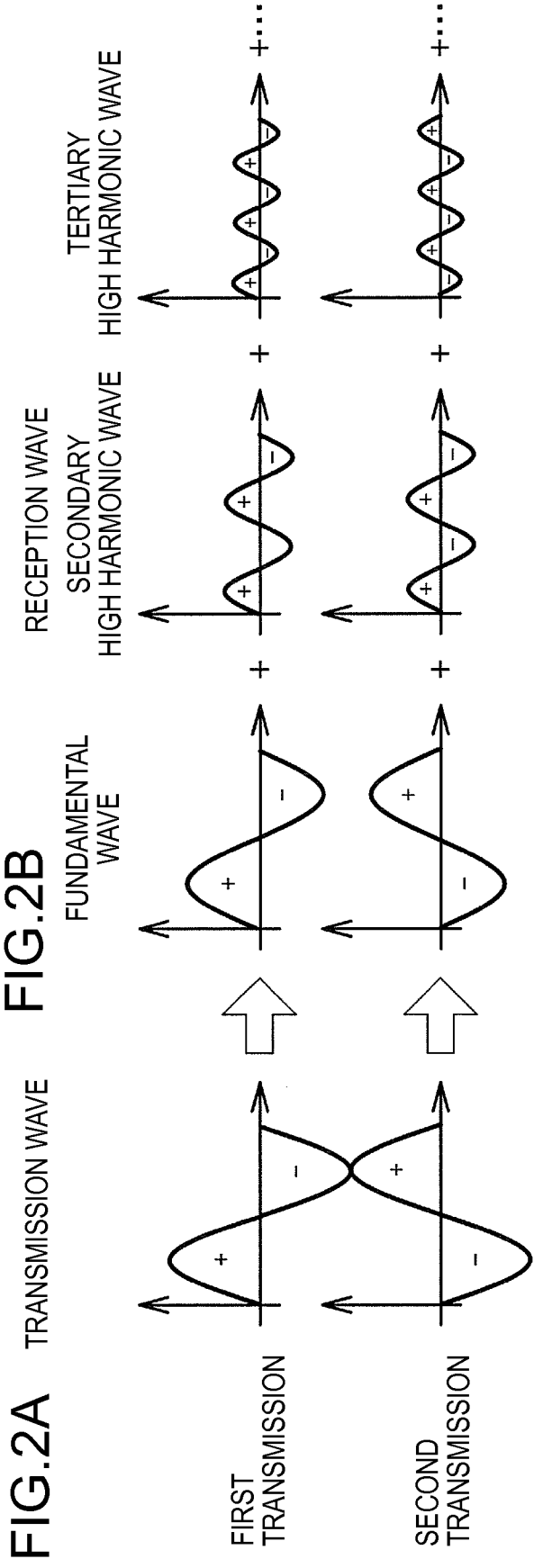

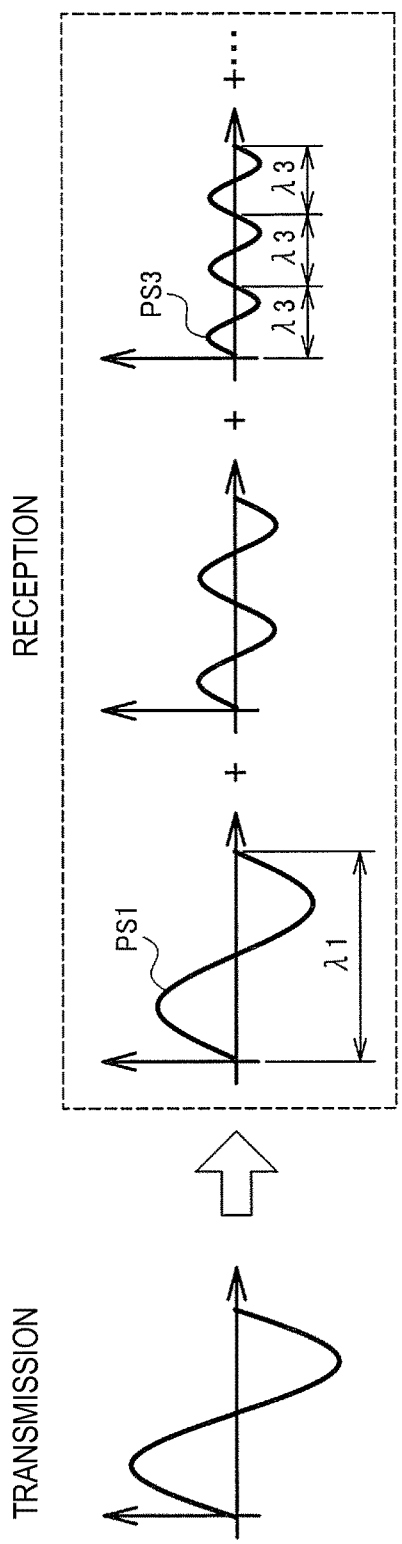
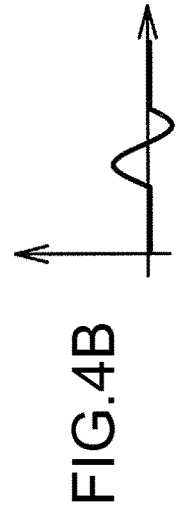
FIG.4A
FIG.4B

FIG.8A
RECEPTION WAVE X
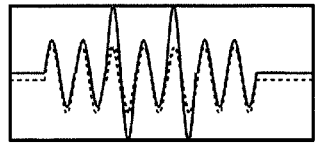
RESOLUTION
FIG.8B
BASIS
FUNCTION $s_i$
(FIRST BASIS WAVE)
COUPLING
COEFFICIENT $a_i$
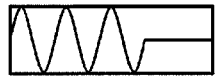 + 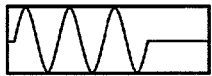 + ⋯ + 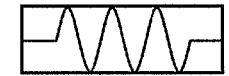
$s_1$        $s_2$        $s_M$
×        ×        ×
$a_1$        $a_2$        $a_M$
CONVERSION
FIG.8C
BASIS
FUNCTION $s'_i$
$\begin{pmatrix} \text{SECOND} \\ \text{BASIS WAVE} \end{pmatrix}$
COUPLING
COEFFICIENT $a_i$
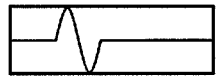 + 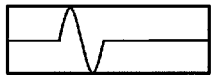 + ⋯ + 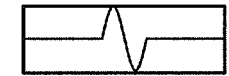
$s'_1$        $s'_2$        $s'_M$
×        ×        ×
$a_1$        $a_2$        $a_M$
RECONFIGURATION
FIG.8D
RECONFIGURATION WAVE X'
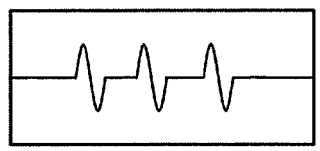

DIFFERENTIAL SIGNAL

SECOND FILTERING PROCESSING

FUNDAMENTAL WAVE COMPONENT

COMPRESSION PROCESSING OF TIME COMPONENT

SECOND BASIS WAVE $\lambda 3 = \frac{\lambda 1}{y}$

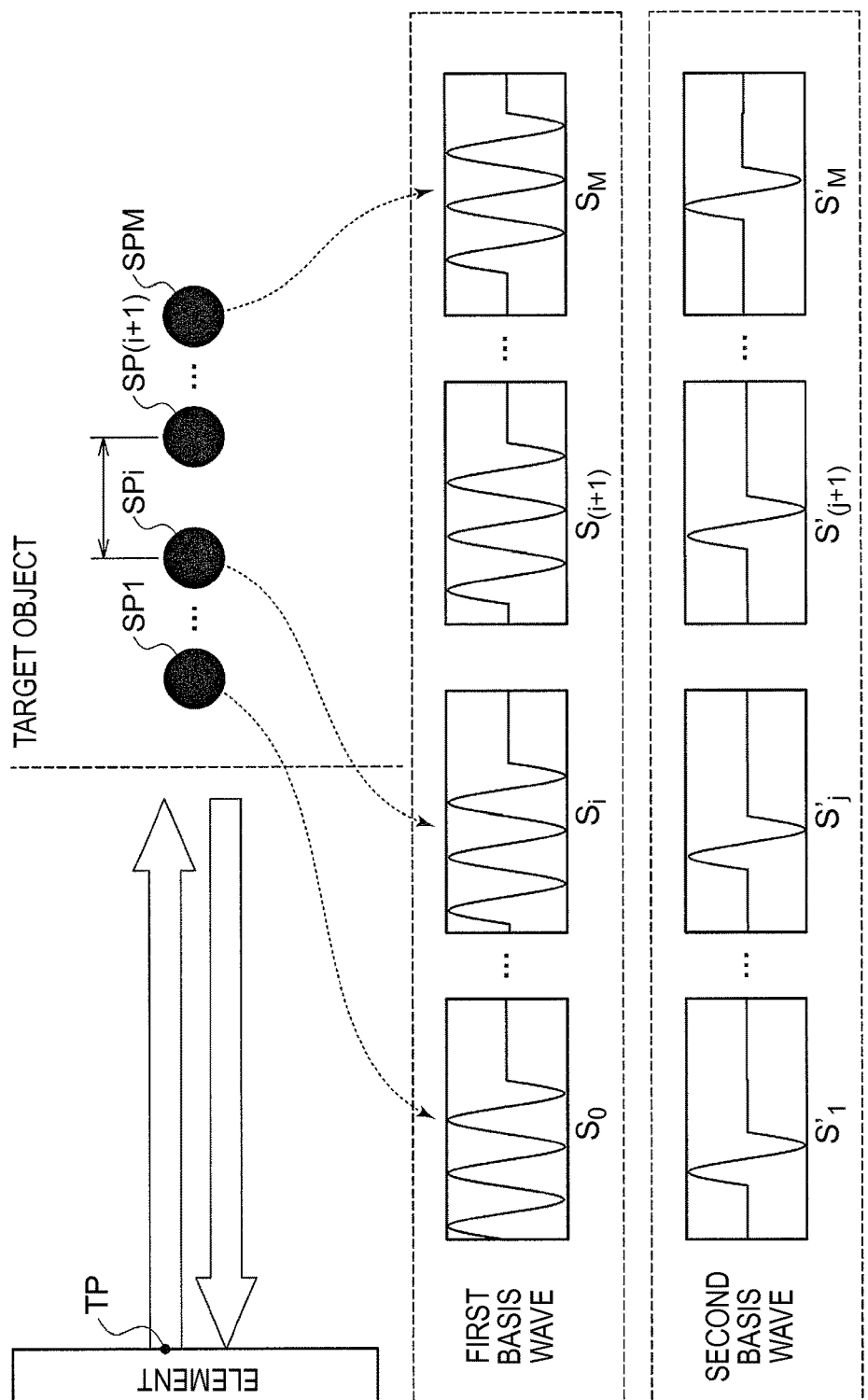

ULTRASONIC MEASUREMENT APPARATUS, ULTRASONIC IMAGING APPARATUS, AND ULTRASONIC MEASUREMENT METHOD

BACKGROUND

1. Technical Field

The present invention relates to an ultrasonic measurement apparatus, an ultrasonic imaging apparatus, and an ultrasonic measurement method.

2. Related Art

As an apparatus used for examining the inside of a human body which is a test object, an ultrasonic measurement apparatus which emits ultrasonic waves toward a target object and receives reflected waves from interfaces having acoustic impedance different from each other inside the target object is gathering attention. Moreover, the ultrasonic measurement apparatus is also applied to image diagnoses of a surface layer of the test object, such as measurement of visceral fat, and measurement of a volume of blood.

When performing the image diagnosis by using such an ultrasonic measurement apparatus, there is a need to achieve high resolving power in image processing of an ultrasonic echo. For example, harmonic imaging (a harmonic imaging method) is utilized.

Here, in the harmonic imaging, a harmonic component of the ultrasonic echo needs to be sampled. However, as a harmonic component sampling method thereof, there are a filtering method and a phase inversion method which is disclosed in JP-A-2002-360569. JP-A-2002-360569 discloses an ultrasonic imaging apparatus that performs the phase inversion method by using high harmonic waves equal to or higher than tertiary harmonic waves.

In B-mode image generation processing in the related art, since distance resolution and azimuthal resolving power are substantially the same as each other, improvement of the distance resolution is not considered as a challenge. However, when harmonic imaging or adaptive-type beam forming is adapted, the azimuthal resolving power becomes higher than the distance resolution, and thus, anisotropy of resolving power newly occurs in a generated image. For example, in JP-A-2002-360569 described above, the distance resolution is relatively degraded with respect to the azimuthal resolving power as well. Therefore, the distance resolution needs to be improved.

SUMMARY

An advantage of some aspects of the invention is to provide an ultrasonic measurement apparatus, an ultrasonic imaging apparatus, and an ultrasonic measurement method in which not only azimuthal resolving power but also distance resolution in a measurement result of a target object obtained by using an ultrasonic wave can be improved.

An aspect of the invention relates to an ultrasonic measurement apparatus including a transmission processing unit that performs processing for transmitting an ultrasonic wave with respect to a target object, a reception processing unit that performs reception processing of an ultrasonic echo with respect to the transmitted ultrasonic wave, and a processing unit that performs processing with respect to a reception signal from the reception processing unit. The processing unit performs coupling coefficient specification processing of a plurality of first basis waves which configure the reception signal, with respect to the reception signal corresponding to a transmission pulse signal which is transmitted by the transmission processing unit. The processing unit performs conversion processing for converting the reception signal into a reconfiguration signal based on a plurality of coupling coefficients which are specified through the coupling coefficient specification processing, and a second basis wave having a number of wave cycles less than that of the first basis wave.

According to the aspect of the invention, the coupling coefficient specification processing of the plurality of first basis waves which configure the reception signal is performed with respect to the reception signal corresponding to the transmission pulse signal which is transmitted. The conversion processing for converting the reception signal into the reconfiguration signal is performed based on the plurality of specified coupling coefficients and the second basis wave having the number of wave cycles less than that of the first basis wave. Therefore, it is possible to improve not only the azimuthal resolving power but also the distance resolution in a measurement result of the target object obtained by using an ultrasonic wave.

In the aspect of the invention, the processing unit may perform the conversion processing after performing the coupling coefficient specification processing of the first basis wave with respect to a high harmonic wave corresponding to the reception signal, and may generate a reconfiguration wave obtained by the second basis wave as the reconfiguration signal.

With this configuration, the reception wave is converted into the reconfiguration wave which is configured to include the second basis wave having the number of wave cycles less than that of the first basis wave, and thus, it is possible to improve the distance resolution in the measurement result of the target object.

In the aspect of the invention, the plurality of first basis waves may amount to M (M is an integer equal to or greater than 2) first basis waves. An ith (i is an integer of $1 \leq i \leq M$) first basis wave among the M first basis waves may be a high harmonic wave corresponding to the reception signal of the ultrasonic wave from an ith point scatterer which is arranged at an ith measurement point. An (i+1)th first basis wave among the M first basis waves may be the high harmonic wave corresponding to the reception signal of the ultrasonic wave from an (i+1)th point scatterer which is arranged at an (i+1)th measurement point at a position farther than the ith measurement point from a transmission point of the ultrasonic wave.

With this configuration, it is possible to sample the first basis wave component from the reception wave with the distance resolution corresponding to a gap between each of the set measurement points.

In the aspect of the invention, the first basis wave may be a high harmonic wave which can be sampled from the reception signal.

With this configuration, it is possible to resolve the reception signal into the plurality of first basis waves.

In the aspect of the invention, the transmission processing unit may transmit two pulse signals having phases mutually inverted to the target object. The processing unit may perform subtraction processing based on two reception signals corresponding to the two transmitted pulse signals, may obtain one differential signal, may perform first filtering processing with respect to the obtained differential signal, may perform sampling of a high harmonic wave component, and may obtain a high harmonic wave as the first basis wave corresponding to a reflected wave component from a point scatterer which is arranged at a given measurement point, based on the sampled high harmonic wave component.

With this configuration, it is possible to specify the first basis wave corresponding to the reflected wave component from the point scatterer at the given measurement point inside the target object.

In the aspect of the invention, the plurality of first basis waves may amount to M (M is an integer equal to or greater than 2) first basis waves. An ith (i is an integer of $1 \leq i \leq M$) first basis wave among the M first basis waves and the (i+1)th first basis wave may be shifted from each other in phase by a phase difference shorter than the phase difference corresponding to a pulse width of the transmission pulse signal or a pulse width of the reception signal.

With this configuration, it is possible to measure the target object with the distance resolution having a distance shorter than the phase difference corresponding to the pulse width of the transmission pulse signal or the pulse width of the reception signal.

In the aspect of the invention, the processing unit may perform the conversion processing based on the plurality of the second basis waves. The plurality of the second basis waves may amount to N (N is an integer equal to or greater than 2) second basis waves. A jth (j is an integer of $1 \leq j \leq N$) second basis wave among the N second basis waves may be a high harmonic wave corresponding to the reception signal of the ultrasonic wave from a jth point scatterer which is arranged at a jth measurement point. A (j+1)th second basis wave among the N second basis waves may be the high harmonic wave corresponding to the reception signal of the ultrasonic wave from a (j+1)th point scatterer which is arranged at a (j+1)th measurement point at a position farther than the jth measurement point from a transmission point of the ultrasonic wave.

With this configuration, it is possible to improve the distance resolution in the measurement result of the target object obtained by using an ultrasonic wave to correspond to the gap between each of the set measurement points.

In the aspect of the invention, the second basis wave may be able to be obtained by performing compression processing of a time component with respect to a fundamental wave which can be sampled from the reception signal.

With this configuration, it is possible to specify the second basis wave through simple processing such as the subtraction processing, the filtering processing, and the compression processing of the time component.

In the aspect of the invention, the transmission processing unit may transmit two pulse signals having phases mutually inverted to the target object. The processing unit may perform subtraction processing based on two reception signals corresponding to the two transmitted pulse signals, may obtain one differential signal, may perform second filtering processing with respect to the obtained differential signal, may perform sampling of a fundamental wave component, may obtain a fundamental wave corresponding to a reflected wave component from a point scatterer which is arranged at a given measurement point, based on the sampled fundamental wave component, may perform compression processing of a time component with respect to the obtained fundamental wave, and may obtain the second basis wave.

With this configuration, it is possible to specify the second basis wave which is obtained by shorten the wavelength of the first basis wave corresponding to the reflected wave component from the point scatterer at the given measurement point inside the target object.

In the aspect of the invention, the second basis wave may have a same phase difference as that of the first basis wave and may have the number of wave cycles less than thereof.

With this configuration, it is possible to shorten the pulse width of the basis wave configuring the reception wave.

In the aspect of the invention, the processing unit may perform envelope detection processing with respect to the reconfiguration signal which is obtained after the conversion processing.

With this configuration, it is possible to cause the display unit to display waveform data by which a user can easily discriminate a measurement result.

In the aspect of the invention, the processing unit may perform deconvolution processing of the reception signal as the coupling coefficient specification processing.

With this configuration, it is possible to specify the coupling coefficient of the first basis wave configuring the reception wave.

In the aspect of the invention, the processing unit may perform convolution processing of the second basis wave as the conversion processing of the reconfiguration signal.

With this configuration, it is possible to generate the reconfiguration wave by using the second basis wave which is obtained by reducing the number of wave cycles of the first basis wave configuring the reception wave or the high harmonic wave that can be sampled from the reception wave.

Another aspect of the invention relates to an ultrasonic imaging apparatus including an ultrasonic measurement apparatus and a display unit that displays image data for displaying generated based on a reconfiguration signal.

Still another aspect of the invention relates to an ultrasonic measurement method including transmitting an ultrasonic wave with respect to a target object; receiving an ultrasonic echo performed with respect to the transmitted ultrasonic wave; performing coupling coefficient specification processing of a plurality of first basis waves which configure a reception signal with respect to the reception signal corresponding to a transmitted transmission pulse signal; and converting the reception signal into a reconfiguration signal based on a plurality of coupling coefficients which are specified through the coupling coefficient specification processing, and a second basis wave having a number of wave cycles less than that of the first basis wave.

BRIEF DESCRIPTION OF THE DRAWINGS

The invention will be described with reference to the accompanying drawings, wherein like numbers reference like elements.

FIGS. 2A to 2C are explanatory diagrams of a phase inversion method.

FIGS. 4A and 4B are explanatory diagrams regarding a relationship between distance resolution and a pulse width.

FIGS. 8A to 8D are explanatory diagrams of generation processing of a reconfiguration wave.

FIGS. 13A to 13C are explanatory diagrams of a correspondence relationship of the point scatterer with respect to the first basis wave and the second basis wave.

DESCRIPTION OF EXEMPLARY EMBODIMENTS

Figure 1:
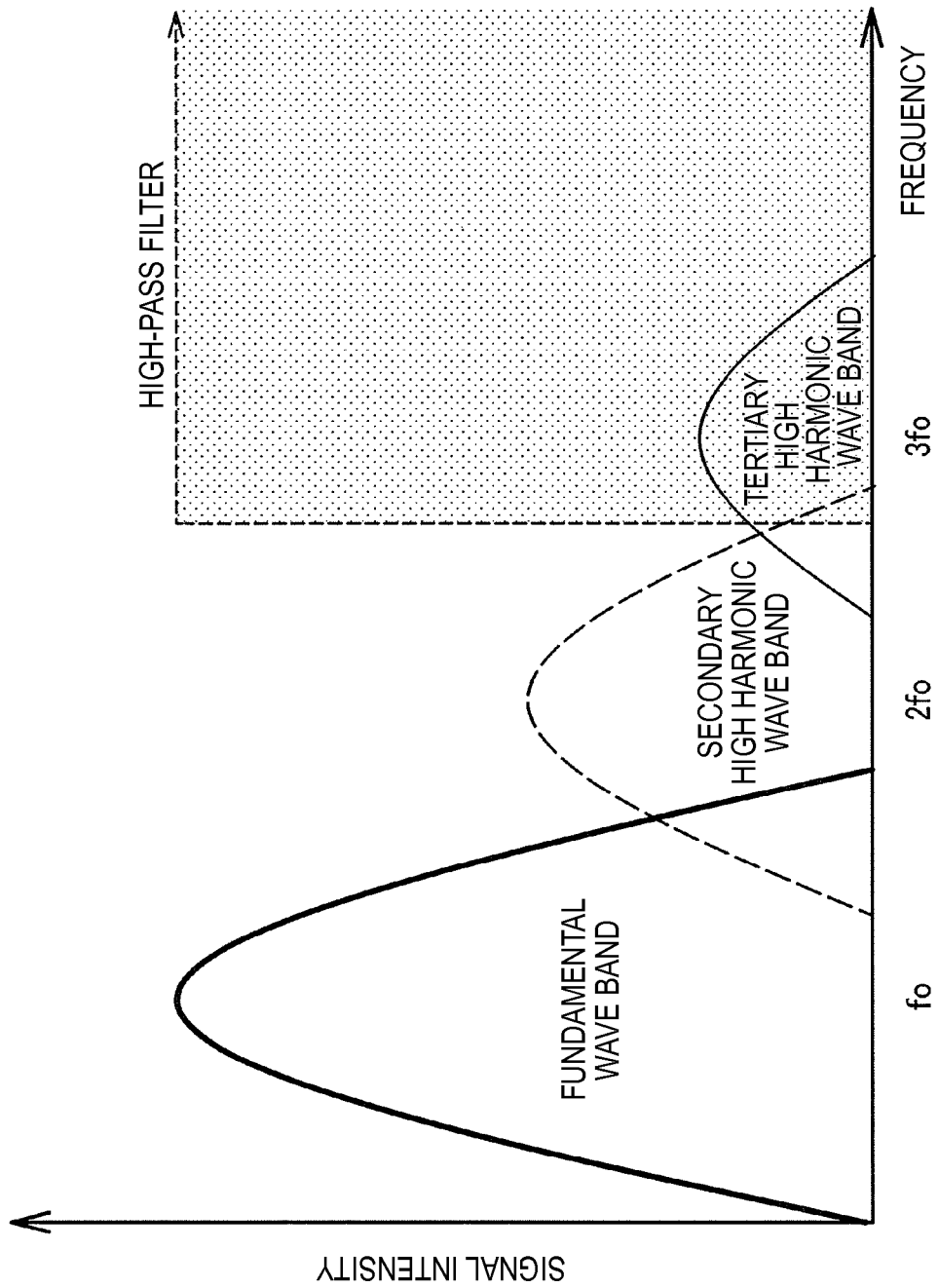
FIG. 1 is an explanatory diagram of a filter method.

Hereinafter, an embodiment will be described. The below-described embodiment does not unjustly limit the contents of the invention disclosed in aspects of the invention. All the configurations described in the embodiment are not necessarily the essential configuration element of the invention.

1. Overview

As an apparatus used for examining the inside of a human body which is a test object, there is a known ultrasonic measurement apparatus which emits ultrasonic waves toward a target object and receives reflected waves from interfaces having acoustic impedance different from each other inside the target object. Moreover, as an application example of the ultrasonic measurement apparatus, there are a pocket-sized ultrasonic viewer and the like which perform image diagnoses of a surface layer of the test object, such as measurement of visceral fat, and measurement of a volume of blood, and are expected to spread out in the field of health care.

As described above, when performing image diagnoses by using such an ultrasonic measurement apparatus, there is a need to achieve high resolving power in image processing of an ultrasonic echo. As technique of the image processing for realizing the high resolving power, there is harmonic imaging (a harmonic imaging method).

The harmonic imaging denotes the technique of imaging a harmonic component described below. Here, a speed of an ultrasonic wave (a compression wave) propagated in a medium has properties of being fast in a portion where sound pressure is high and being slow in a portion where the same is low. Therefore, even in a simple sine wave, distortion is gradually generated in a propagation process and the waveform varies, thereby including a high harmonic wave component (also referred to as a harmonic component or a nonlinear component) which is the integer multiple of a fundamental frequency not included in a fundamental wave. Such a nonlinear effect increases in proportion to the square of the sound pressure of the ultrasonic wave, and is accumulated in proportion to a propagation distance.

The harmonic imaging is broadly divided into two types such as tissue harmonic imaging in which a harmonic component generated by the tissue itself when ultrasonic waves are propagated in the tissues is imaged, and contrast harmonic imaging in which a harmonic component generated when micro bubbles of an ultrasonic contrast agent resonate or burst is imaged. The tissue harmonic imaging is used in the embodiment.

There are two advantages in the harmonic imaging. First, since the amplitude of the harmonic component has characteristics of being proportional to the square of the amplitude of a transmitted ultrasonic wave, the amplitude of the harmonic component becomes strong at the center of a transmission beam where the sound pressure is high and becomes weak rapidly as being away from the center of the beam to the edge. Accordingly, in the harmonic imaging, the range in which the nonlinear effect occurs is limited to the center of the beam. As a result, azimuthal resolving power is improved compared to other types of technique. This is the first advantage thereof.

As major noise appears in an ultrasonic image, there are noise caused by multiple reflections and noise caused by a side lobe. Here, a reflected ultrasonic echo has low sound pressure so that there is no generation of the harmonic component itself. Therefore, the noise caused by the multiple reflections is reduced. Moreover, the side lobe has low sound pressure, and there is no generation of the harmonic component itself even in the side lobe. Therefore, the noise caused by the side lobe is also reduced. In this manner, in the harmonic imaging, it is possible to reduce the noise caused by the multiple reflections, and the noise caused by the side lobe as well. This is the second advantage thereof.

According to the embodiment, tertiary harmonic imaging for imaging a tertiary high harmonic wave component is performed among the types of the harmonic imaging. Since the beam width becomes thin in the tertiary harmonic imaging with respect to the technique of imaging a secondary high harmonic wave component, it is possible to improve the azimuthal resolving power further.

Here, in the tertiary harmonic imaging, there is a need to perform sampling of the tertiary high harmonic wave component of the ultrasonic echo. As methods of sampling thereof, there are a filtering method and a phase inversion method.

First, the filtering method is technique in which a fundamental wave component, the secondary high harmonic wave component, and the tertiary high harmonic wave component are separated from one another by using a frequency filter (a high-pass filter), and only the tertiary high harmonic wave component is sampled and imaged. For example, as a diagram illustrating the filtering method, the graph in FIG. 1 illustrates a reception signal of which the center frequency of a fundamental wave band is $f_0$, the center frequency of a secondary high harmonic wave band is $2f_0$, and the center frequency of a tertiary high harmonic wave band is $3f_0$, while having the vertical axis as the signal intensity and the horizontal axis as the frequency. As illustrated in FIG. 1, since each of the fundamental wave component, the secondary high harmonic wave component, and the tertiary high harmonic wave component to be received has a certain bandwidth, the secondary high harmonic wave component and the tertiary high harmonic wave component overlap with each other so that both thereof cannot be separated from each other, thereby leading to a cause of image deterioration. There is a need to lengthen the pulse width in order to minimize the overlapping. However, when the pulse width is lengthened, distance resolution is degraded.

Meanwhile, the phase inversion method is technique which is developed so as to improve weak points of the filtering method. The technique performs transmission of ultrasonic waves twice in a row in the same direction. As illustrated in FIG. 2A, the second transmission wave has the phase which is different from that of the first transmission wave by 180 degrees.

A returned reception wave which is reflected by a living body or a contrast agent includes a harmonic component due to nonlinear propagation characteristics thereof, thereby having a distorted waveform. FIG. 2B illustrates a case where a reception wave with respect to a transmission wave for each time is resolved into a fundamental wave, a secondary high harmonic wave, and a tertiary high harmonic wave. As illustrated in FIG. 2B, since the first and second transmission waves are inverted for the reception waves from two times of transmissions, there exists a relationship in which the fundamental wave component and the odd-ordered high harmonic wave component (the tertiary high harmonic wave component) are inverted, but the even-ordered high harmonic wave component (the secondary high harmonic wave component) is not inverted. In other words, in the reception waves from two times of receptions with respect to the transmission waves from two times of transmissions, the fundamental wave component and the odd-ordered high harmonic wave component are mutually inverted in phase, but the even-ordered high harmonic wave component retains the same phase.

Therefore, when subtraction is performed for the reception waves from two times of receptions, the secondary high harmonic wave component is eliminated as illustrated in FIG. 2C, and the fundamental wave component and the tertiary high harmonic wave component remain while having the amplitudes increased twice. Accordingly, the fundamental wave component and the tertiary high harmonic wave component can be sampled.

Figure 3A:
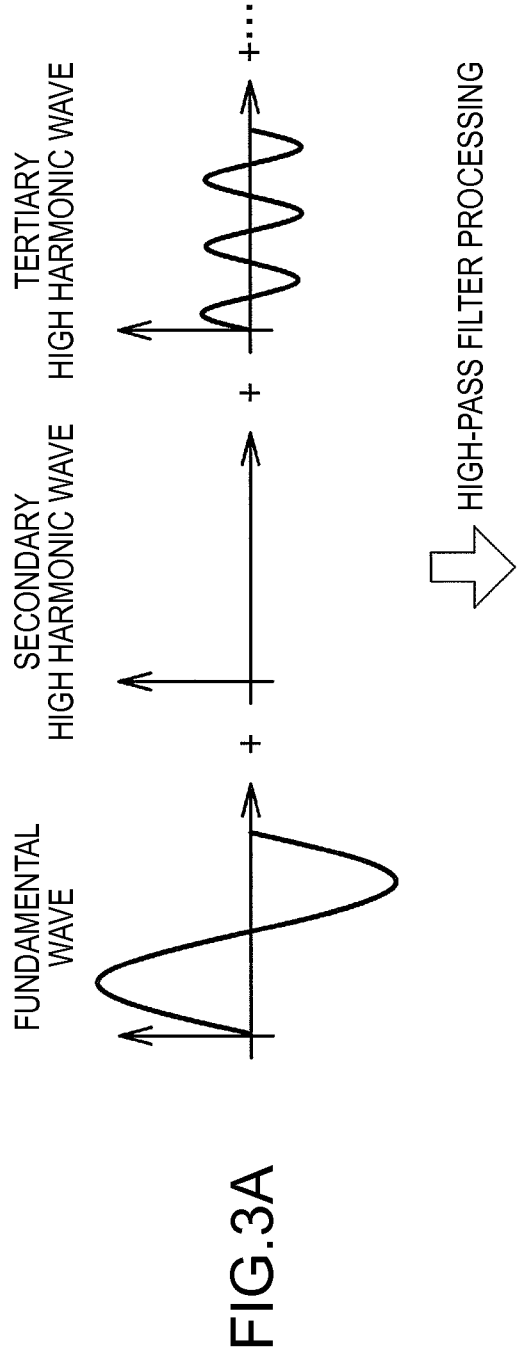
FIGS. 3A and 3B are explanatory diagrams of processing in which the phase inversion method and filtering processing are used together.
Figure 3B:
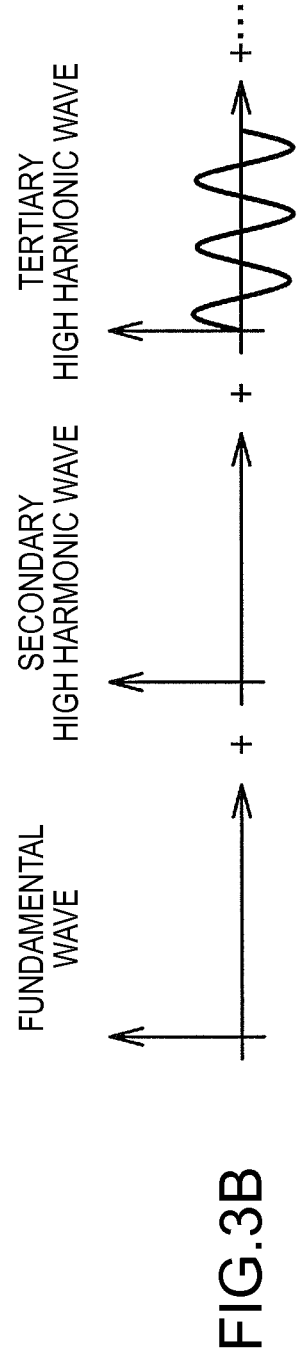

Moreover, when performing sampling of only an N-ordered high harmonic wave component which is targeted among the fundamental wave component, the odd-ordered high harmonic wave component, and the even-ordered high harmonic wave component which are sampled by the phase inversion method (N is an integer equal to or greater than 2), the phase inversion method needs to be combined with the above-described filtering method. According to the embodiment, the fundamental wave component and the tertiary high harmonic wave component are separated by using the frequency filter (the high-pass filter or a band-pass filter) from the fundamental wave component and the tertiary high harmonic wave component which are sampled by the phase inversion method as illustrated in FIG. 3A, and only the tertiary high harmonic wave component is sampled and imaged as illustrated in FIG. 3B.

In this manner, as the phase inversion method and the filtering method are used together, it is possible to generate a high-quality B-mode image having less artifacts caused by the side lobe or multiple reflections and having the improved azimuthal resolving power compared to the technique of generating the B-mode image from only the fundamental wave component in the related art.

However, even when the B-mode image is generated by the above-described method, the distance resolution is not improved. A distance resolution $\Delta x$ is decided depending on the pulse width and is obtained by the following Expression 1. In the following Expression 1, the factor n is a number of wave cycles and the factor $\lambda$ is the wavelength.

$$\Delta x = \frac{n\lambda}{2} \quad (1)$$

For example, in the reception wave with respect to the transmission wave illustrated in FIG. 4A, a wavelength $\lambda 3$ of a tertiary high harmonic wave component PS3 becomes ⅓ compared to a wavelength $\lambda 1$ of a fundamental wave component PS1. However, a number of wave cycles n3 of the tertiary high harmonic wave component PS3 becomes three times a number of wave cycles n1 of the fundamental wave component PS1. Therefore, even though an image is generated by using the tertiary high harmonic wave component, there is no change in the distance resolution $\Delta x$ compared to a case of using the fundamental wave component. As illustrated in FIG. 4B, if a wave which is smaller than the fundamental wave component in both wavelength and number of wave cycles can be used, it is possible to improve the distance resolution.

According to the embodiment described below, coupling coefficient specification processing of a plurality of first basis waves which configure the reception signal is performed with respect to the reception signal of the ultrasonic wave, and conversion processing for converting the reception signal into a reconfiguration signal is performed based on a plurality of specified coupling coefficients, and a second basis wave having the number of wave cycles less than that of the first basis wave. In other words, according to the embodiment, a reception wave X illustrated in the below-described FIG. 8A is reconfigured so as to generate a reconfiguration wave X' illustrated in FIG. 8D. The reconfiguration wave X is configured to include the second basis wave illustrated in FIG. 8C. The second basis wave has the same wavelength and has the less number of wave cycles compared to the first basis wave in FIG. 8B configuring the original reception wave X. Therefore, it is possible to improve the distance resolution.

2. Example of System Configuration

Figure 5:
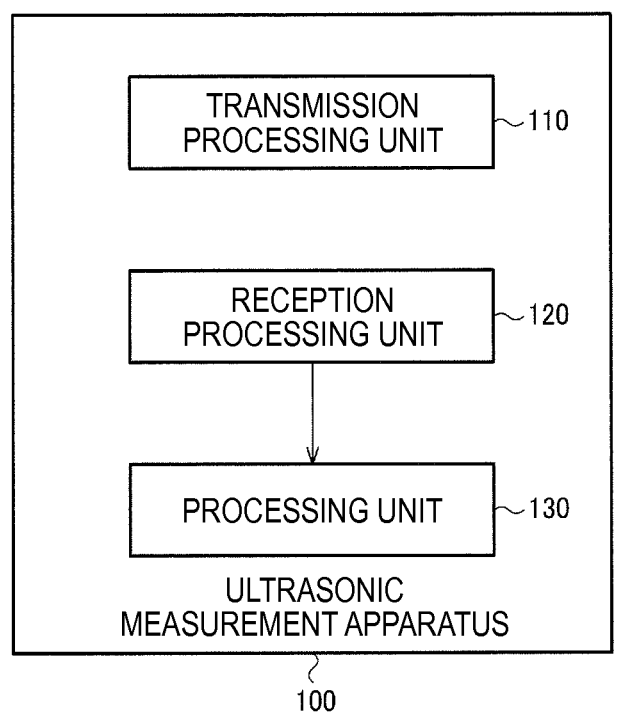
FIG. 5 is an example of a system configuration of an embodiment.

Subsequently, FIG. 5 illustrates a configuration example of the ultrasonic measurement apparatus of the embodiment. An ultrasonic measurement apparatus 100 includes a transmission processing unit 110, a reception processing unit 120, and a processing unit 130.

Figure 6:
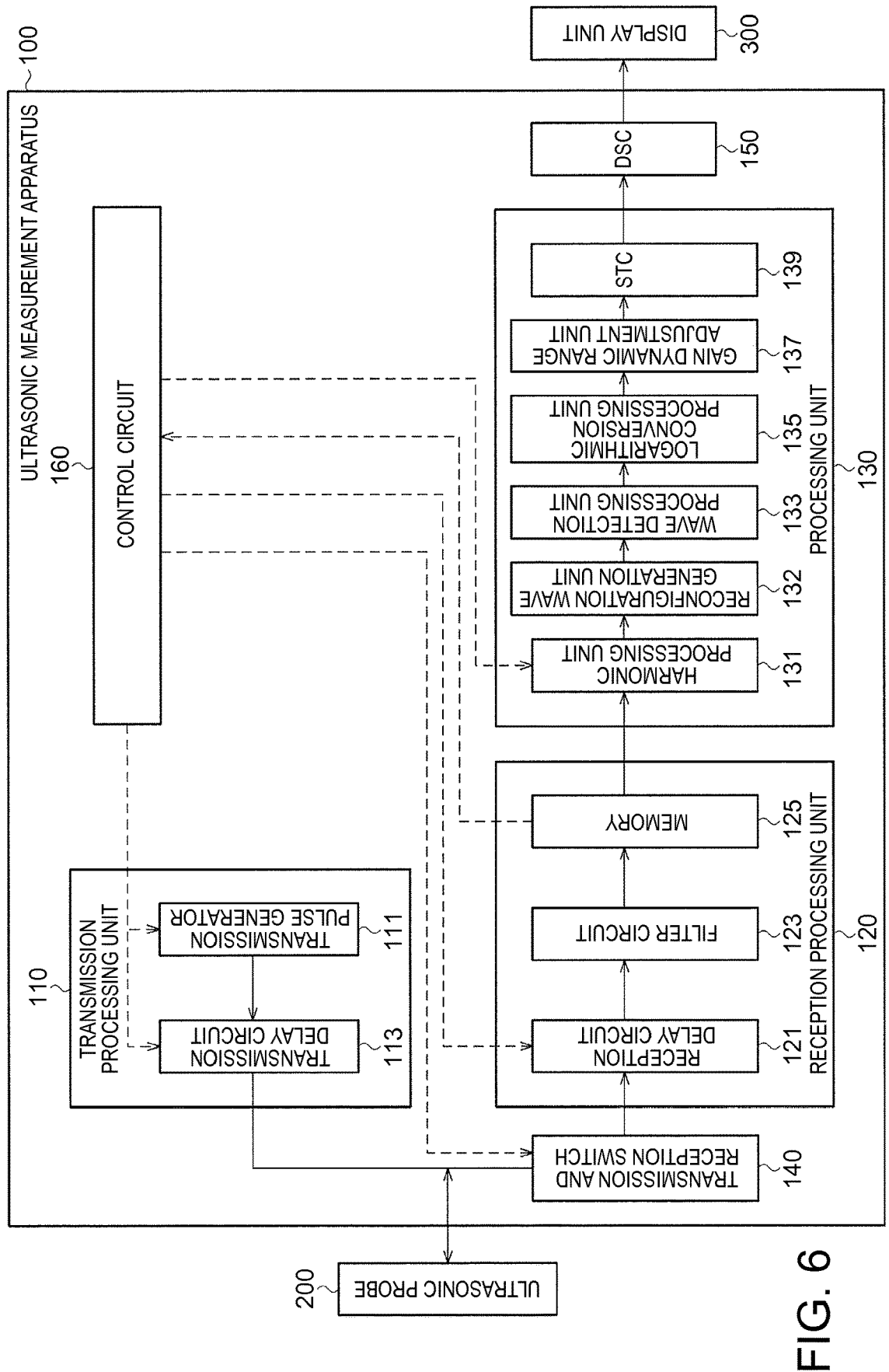
FIG. 6 is an example of a detailed system configuration of an ultrasonic imaging apparatus of the embodiment.

Moreover, FIG. 6 illustrates a specific configuration example of an ultrasonic imaging apparatus of the embodiment. The ultrasonic imaging apparatus includes the ultrasonic measurement apparatus 100, an ultrasonic probe 200, and a display unit 300. The ultrasonic measurement apparatus 100 illustrated in FIG. 6 includes the transmission processing unit 110, the reception processing unit 120, the processing unit 130, a transmission and reception switch 140, a digital scan convertor (DSC) 150, and a control circuit 160.

The ultrasonic measurement apparatus 100 and the ultrasonic imaging apparatus including thereof are not limited to the configurations in FIGS. 5 and 6, and various modifications can be executed by omitting a portion of the configuration elements thereof or adding other configuration elements thereto. In addition, a portion or all of the functions of the ultrasonic measurement apparatus 100 of the embodiment and the ultrasonic imaging apparatus including thereof may be realized by a server which is connected through communication.

Subsequently, descriptions will be given regarding processing performed by each of units.

The ultrasonic probe 200 includes an ultrasonic transducer device.

The ultrasonic transducer device transmits an ultrasonic beam to a target object while scanning the target object along a scanning surface and receives an ultrasonic echo of the ultrasonic beam. In an example of a type thereof using a piezoelectric element, the ultrasonic transducer device includes the plurality of ultrasonic transducer elements (an ultrasonic element array), and a substrate in which a plurality of the apertures are arranged in an array shape. An element having a monomorph (unimorph) structure in which a thin piezoelectric element and a metal plate (a vibration film) are pasted together is used as the ultrasonic transducer element. The ultrasonic transducer element (a vibration element) converts electrical vibration into mechanical vibration. However, in this case, when the piezoelectric element expands and contracts within the surface, since the measurements of the pasted metal plate (the vibration film) do not change, there is an occurrence of a warp.

In the ultrasonic transducer device, one channel may be configured to include several ultrasonic transducer elements which are arranged to be adjacent to one another, and an ultrasonic beam may be sequentially moved while driving a plurality of the channels at a time.

A transducer in a type using the piezoelectric element (a thin film piezoelectric element) can be employed as the ultrasonic transducer device. However, the embodiment is not limited thereto. For example, a transducer in a type using a capacitive element such as a capacitive micro-machined ultrasonic transducer (c-MUT) may be employed, or a bulk-type transducer may be employed. The ultrasonic transducer element and the ultrasonic transducer device will be described later further in detail.

The transmission processing unit 110 performs processing for transmitting an ultrasonic wave to a target object. For example, the transmission processing unit 110 illustrated in FIG. 6 includes a transmission pulse generator 111 and a transmission delay circuit 113.

Specifically, the transmission pulse generator 111 applies a transmission pulse voltage and drives the ultrasonic probe 200.

The transmission delay circuit 113 performs focusing of a transmission beam. Therefore, the transmission delay circuit 113 applies a differential time between channels regarding the timing of applying the transmission pulse voltage, thereby focusing the ultrasonic waves generated by a plurality of vibration elements. In this manner, it is possible to arbitrarily change the focal distance by varying the delay time.

The transmission and reception switch 140 performs switching processing for transmitting and receiving an ultrasonic wave. The transmission and reception switch 140 protects amplitude pulses during a transmission from being input to a reception circuit, and allows a signal during a reception to pass through the reception circuit.

Meanwhile, the reception processing unit 120 performs reception processing of an ultrasonic echo with respect to a transmitted ultrasonic wave. For example, the reception processing unit 120 illustrated in FIG. 6 includes a reception delay circuit 121, a filter circuit 123, and a memory 125.

The reception delay circuit 121 performs focusing of a reception beam. Since a reflected wave from a certain reflector spreads on a spherical surface, the reception delay circuit 121 applies the delay time so as to cause the times taken for arriving at each of the vibrators to be the same, thereby adding the reflected wave inconsideration of the delay time.

The filter circuit 123 performs filtering processing with respect to the reception signal by using the band-pass filter, thereby eliminating the noise.

The memory 125 stores the reception signal output from the filter circuit 123, and the function thereof can be realized by using a memory, for example, RAM, or HDD.

The processing unit 130 performs processing with respect to the reception signal from the reception processing unit 120. For example, the processing unit 130 illustrated in FIG. 6 includes a harmonic processing unit 131, a reconfiguration wave generation unit 132, a wave detection processing unit 133, a logarithmic conversion processing unit 135, a gain dynamic range adjustment unit 137, and a sensitivity time control (STC) 139.

Specifically, as described above, the harmonic processing unit 131 performs sampling processing of the harmonic component (mainly, the tertiary high harmonic wave component).

As described below, the reconfiguration wave generation unit 132 performs the conversion processing for converting the reception signal into the reconfiguration signal based on the sampled harmonic component (mainly, the tertiary high harmonic wave component).

The wave detection processing unit 133 sets a low-pass filter after performing absolute value (rectification) processing, thereby sampling an unmodulated signal.

Moreover, the logarithmic conversion processing unit 135 performs compression of log, thereby converting the form of expression so as to cause the maximum portion and the minimum portion of the signal intensity of the reception signal can be easily checked at the same time.

The gain dynamic range adjustment unit 137 adjusts the signal intensity and the region of interest. Specifically, in gain adjustment processing, a direct-current component is added to an input signal after being subjected to the compression of log. In dynamic range adjustment processing, the input signal after being subjected to the compression of log is multiplied by an arbitrary number.

The STC 139 corrects an amplification degree (brightness) in accordance with the depth, thereby acquiring an image having uniform brightness throughout an image in the entirety thereof.

The functions of the processing unit 130 can be realized by using hardware such as various processors (CPU and the like) and ASIC (a gate array and the like), or a program.

The DSC 150 performs scanning conversion processing with respect to B-mode image data. For example, the DSC 150 converts a line signal into an image signal through interpolation processing such as a bilinear method.

The control circuit 160 controls the transmission pulse generator 111, the transmission delay circuit 113, the reception delay circuit 121, the transmission and reception switch 140, and the harmonic processing unit 131.

The display unit 300 displays image data for displaying generated based on the reconfiguration signal. For example, the display unit 300 may be realized by a liquid crystal display, an organic EL display, an electronic paper, or the like.

Figure 7A:
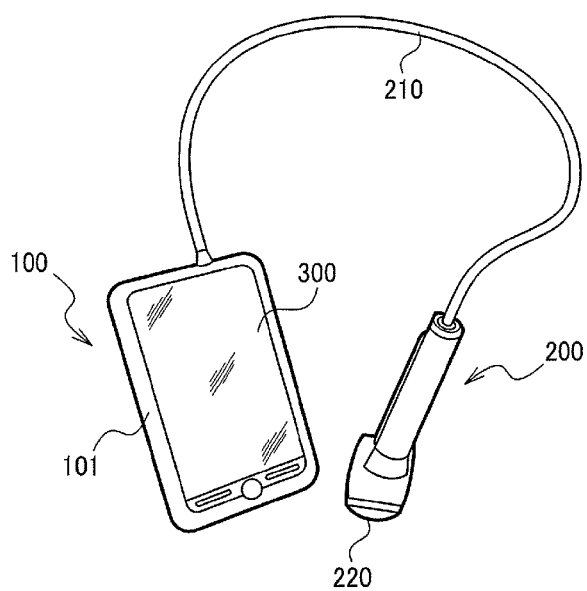
FIGS. 7A to 7C are examples of a specific instrument configuration of an ultrasonic measurement apparatus.
Figure 7C:
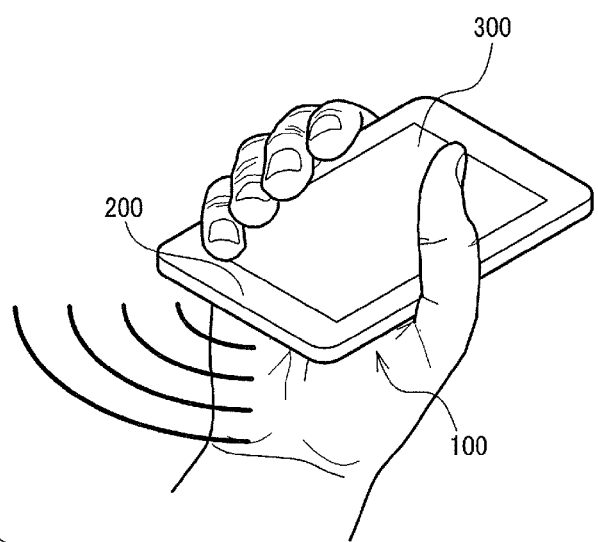
Figure 7B:
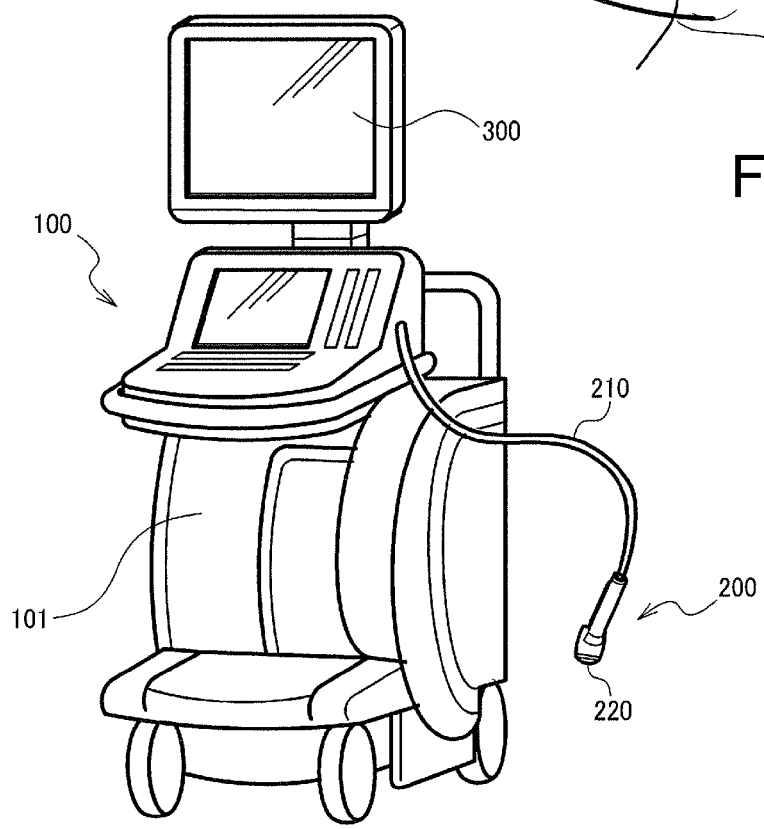

Here, FIGS. 7A to 7C illustrate specific examples of configurations of the instruments in the ultrasonic imaging apparatus (in a broad sense, an electronic instrument) of the embodiment. FIG. 7A is an example of a portable ultrasonic imaging apparatus, and FIG. 7B is an example of a stationary ultrasonic imaging apparatus. FIG. 7C is an example of an integrated ultrasonic imaging apparatus equipped with the built-in ultrasonic probe 200.

The ultrasonic imaging apparatus in FIGS. 7A and 7B includes the ultrasonic probe 200 and the ultrasonic measurement apparatus 100. The ultrasonic probe 200 and the ultrasonic measurement apparatus 100 are connected to each other by a cable 210. A probe head 220 is provided at the tip end portion of the ultrasonic probe 200, and the display unit 300 for displaying an image is provided in an ultrasonic measurement apparatus main body 101. In FIG. 7C, the ultrasonic probe 200 is built in the ultrasonic imaging apparatus having the display unit 300. In a case of FIG. 7C, the ultrasonic imaging apparatus can be realized by a general-purpose portable information terminal, for example, a smartphone.

3. Details of Processing 3.1. Generation Processing of Reconfiguration Wave

The processing unit 130 of the embodiment performs the coupling coefficient specification processing of the plurality of first basis waves which configure the reception signal, with respect to the reception signal corresponding to the transmission pulse signal which is transmitted by the transmission processing unit 110. The processing unit 130 performs the conversion processing for converting the reception signal into the reconfiguration signal based on the plurality of coupling coefficients specified through the coupling coefficient specification processing, and the second basis wave having the number of wave cycles less than that of the first basis wave.

Accordingly, the inside of the target object can be measured based on the generated reconfiguration signal. The reconfiguration signal is configured to include the second basis wave having the number of wave cycles less than that of the first basis wave. The number of wave cycles of the first basis wave and the number of wave cycles of the second basis wave are not necessarily natural numbers, and may be 1.5 waves, for example.

Here, the reconfiguration signal (the reconfiguration wave) is a signal obtained by causing each of the reflected signal components (the reflected wave components) from each of point scatterers inside the target object while being included in the reception signal (the reception wave) to be replaced with the signal (the waveform) having the pulse width shorter than that of the original reflected signal component, and causing the signal (the waveform) after the replacement to overlap again with the original reflected signal component at the same timing as the reception timing thereof. For example, the reconfiguration signal is the reconfiguration wave illustrated in FIG. 8D described below. In other words, the above-described first basis wave corresponds to each of the reflected signal components (the reflected wave components) from each of the point scatterers, and the second basis wave corresponds to the signal (the waveform) having the pulse width shorter than the original reflected signal component which replaces the first basis wave.

The first basis wave is a wave corresponding to the reflected wave component from the point scatterer which exists at the given depth inside the target object, among the reception signals. For example, the first basis wave is a wave illustrated in FIG. 8B described below. As described below, it is possible to determine whether or not the point scatterer corresponding to the first basis wave thereof is included in the target object by determining whether or not the first basis wave component is included in the reception signal. When it can be determined that the point scatterer corresponding to the first basis wave thereof is included in the target object, reflection characteristics such as the point scatterer can be specified based on the signal intensity (reflection intensity) of the first basis wave component included in the reception signal. The processing of specifying the reflection intensity is the coupling coefficient specification processing. The second basis wave will be described later.

In this manner, according to the embodiment, since each of the reflected wave components of the reception wave is replaced with the second basis wave having the shorter pulse width and the reception wave is reconfigured, it is possible to improve the distance resolution in the measurement result of the target object based on the reconfiguration signal.

Therefore, it is possible to improve not only the azimuthal resolving power but also the distance resolution in a measurement result of the target object obtained by using an ultrasonic wave.

Specifically, after performing the coupling coefficient specification processing of a first basis wave ($S_i$) as illustrated in FIG. 8B with respect to the high harmonic wave (the reception wave X) corresponding to the reception signal as illustrated in FIG. 8A for example, the processing unit 130 performs the conversion processing for converting the first basis wave ($S_i$) into a second basis wave ($S'_i$) which configures the reception wave X as illustrated in FIG. 8C, thereby generating the reconfiguration wave X' based on the second basis wave ($S'_i$) as the reconfiguration signal as illustrated in FIG. 8D. The high harmonic wave X illustrated in FIG. 8A may be the high harmonic wave and the like which are sampled by performing the filtering processing with respect to the original reception wave.

Accordingly, it is possible to convert the reception wave into the reconfiguration wave which is configured to include the second basis wave having the number of wave cycles less than that of the first basis wave, and thus, the distance resolution in the measurement result of the target object can be improved.

Here, the first basis wave is a high harmonic wave which can be sampled from the reception signal. Accordingly, it is possible to resolve the reception signal into the plurality of first basis waves.

For example, according to the example in FIG. 8B, the first basis wave is a wave represented by a basis function $S_i$. According to the embodiment, the first basis wave is not one but a plurality of waves. For example, according to the example in FIG. 8B, the plurality of first basis waves are considered to amount M first basis waves. The factor M is an integer equal to or greater than 2, and the factor i is an integer of $1 \le i \le M$.

An ith first basis wave among the M first basis waves and an (i+1)th first basis wave are shifted from each other in phase by a phase difference shorter than the phase difference corresponding to the pulse width of the transmission pulse signal or the pulse width of the reception signal.

Accordingly, it is possible to measure the target object with the distance resolution at a distance shorter than the phase difference corresponding to the pulse width of the transmission pulse signal or the pulse width of the reception signal.

Moreover, when the coupling coefficient specification processing of the plurality of first basis waves which configure the reception wave X is performed, as illustrated in FIG. 8B, each of coupling coefficients $a_i$ can be obtained with respect to each of the first basis waves $S_i$. The coupling coefficient $a_i$ is a value for deciding the ratio of the corresponding first basis wave $S_i$ included in the reception wave X. In other words, as shown in the following Expression 2, the reception wave X is presented by the sum of the products between each of the first basis waves and each of the coupling coefficients.

$$X = \sum_{i=1}^{M} (s_i \cdot a_i) \tag{2}$$

The second basis wave is a wave which has the same phase difference and has the less number of wave cycles compared to the first basis wave. The phase difference denotes a phase difference between the ith first basis wave and the (i+1)th first basis wave.

Each of the coupling coefficients $a_i$ obtained when the reception wave X is resolved into the plurality of first basis waves $S_i$ (the coupling coefficient specification processing) is caused to correspond to each of the second basis waves $S'_i$. Accordingly, the reception wave X is presented by the following Expression 3.

$$X' = \sum_{i=1}^{M} (s'_i \cdot a'_i) \quad (3)$$

Accordingly, it is possible to shorten the pulse width of the basis wave configuring the reception wave.

Subsequently, a flow of processing of the embodiment will be described with reference to the flow chart of FIG. 9.

First, the initial value of a scanning line number n is set to 1 (S101).

Subsequently, the transmission pulse generator 111 generates a pulse voltage of phase 0° (S102).

The transmission delay circuit 113 performs transmission focus controlling (S103), and the ultrasonic probe 200 emits an ultrasonic beam corresponding to the generated pulse voltage with respect to the target object (S104). Moreover, the ultrasonic probe 200 receives an ultrasonic echo which is generated when the emitted ultrasonic beam is reflected by the target object and returns (S104).

In contrast, the reception delay circuit 121 performs reception focus controlling (S105). The filter circuit 123 performs band-pass filter (BPF) processing with respect to the reception signal after the reception focus controlling is performed (S106), and the reception signal after being subjected to the BPF processing is retained in the memory 125 (S107).

Subsequently, the transmission pulse generator 111 generates a pulse voltage of phase 180° (S108). The steps of processing similar to those from Steps S102 to S107 described above are performed with respect to the pulse after being subjected to the phase inversion (S109 to S113).

Thereafter, it is determined whether or not the processing from Steps S102 to S113 is performed throughout all of the scanning lines (S114). Specifically, it is determined whether or not the current scanning line number n is smaller than all of the scanning line numbers N.

When it is determined that the processing from Steps S102 to S113 is not performed throughout all of the scanning lines, that is, when it is determined that the current scanning line number n is smaller than all of the scanning line numbers N, 1 is added to the current scanning line number n (S115), and the processing from Steps S102 to S114 is performed again.

Meanwhile, in Step S115, when it is determined that the processing from Steps S102 to S114 is performed throughout all of the scanning lines, that is, when it is determined that the current scanning line number n is equivalent to all of the scanning line numbers N, the harmonic processing unit 131 performs the sampling processing of the high harmonic wave component (the harmonic component) (S116). Specifically, in the sampling processing, as described in FIGS. 2A to 2C, subtraction processing is performed with respect to the reception wave corresponding to the transmission wave of phase 0° and the reception wave corresponding to the transmission wave of phase 180°, thereby sampling the fundamental wave and the tertiary high harmonic wave. Thereafter, as illustrated in FIGS. 3A and 3B, the high-pass filtering processing is performed with respect to the fundamental wave and the tertiary high harmonic wave which are sampled, thereby sampling only the tertiary high harmonic wave.

Subsequently, the reconfiguration wave generation unit 132 generates the reconfiguration wave based on the sampled tertiary high harmonic wave (S117). Here, a flow of generation processing of the reconfiguration wave according to the embodiment is illustrated in the flow chart of FIG. 10.

First, the reconfiguration wave generation unit 132 reads the basis functions (the first basis wave and the second basis wave) from the memory (not illustrated) (S201). Subsequently, the reconfiguration wave generation unit 132 performs frequency filtering processing (BPF), thereby sampling the first basis wave component in the tertiary high harmonic wave based on the first basis wave read out from the memory as illustrated in FIG. 8B described above (S202).

The reconfiguration wave generation unit 132 performs specification processing of the coupling coefficient of the first basis wave which configures the tertiary high harmonic wave, based on the sampling result (S203).

Specifically, the reconfiguration wave generation unit 132 (the processing unit 130) performs deconvolution processing of the reception signal, as the coupling coefficient specification processing.

Accordingly, it is possible to specify the coupling coefficient of the first basis wave which configures the reception wave.

Thereafter, the reconfiguration wave generation unit 132 replaces each of the first basis waves with the second basis wave having the same phase, thereby generating the reconfiguration wave based on the coupling coefficient and the second basis wave which are specified (S204). In other words, the conversion processing for converting the reception signal into the reconfiguration signal is performed.

Specifically, the processing unit 130 performs convolution processing of the second basis wave, as the conversion processing of the reconfiguration signal.

Accordingly, it is possible to generate the reconfiguration wave based on the second basis wave obtained by reducing the number of wave cycles of the first basis wave configuring the high harmonic wave which can be sampled from the reception wave or the reception wave.

After the wave detection processing unit 133 performs the absolute value (rectification) processing with respect to the generated reconfiguration wave, the low-pass filter is set, the unmodulated signal is sampled (S118), and the logarithmic conversion processing unit 135 performs logarithmic conversion processing (S119).

The gain dynamic range adjustment unit 137 adjusts signal intensity and the region of interest (S120), and the STC 139 corrects the amplification degree (brightness) in accordance with the depth thereof (S121).

Moreover, the DSC 150 performs the scanning conversion processing and generates B-mode image data (image data for displaying) (S122). The display unit 300 displays the generated image data for displaying (S123), and then, the processing ends.

3.2. Generation Processing of First Basis Wave and Second Basis Wave

Figure 9:
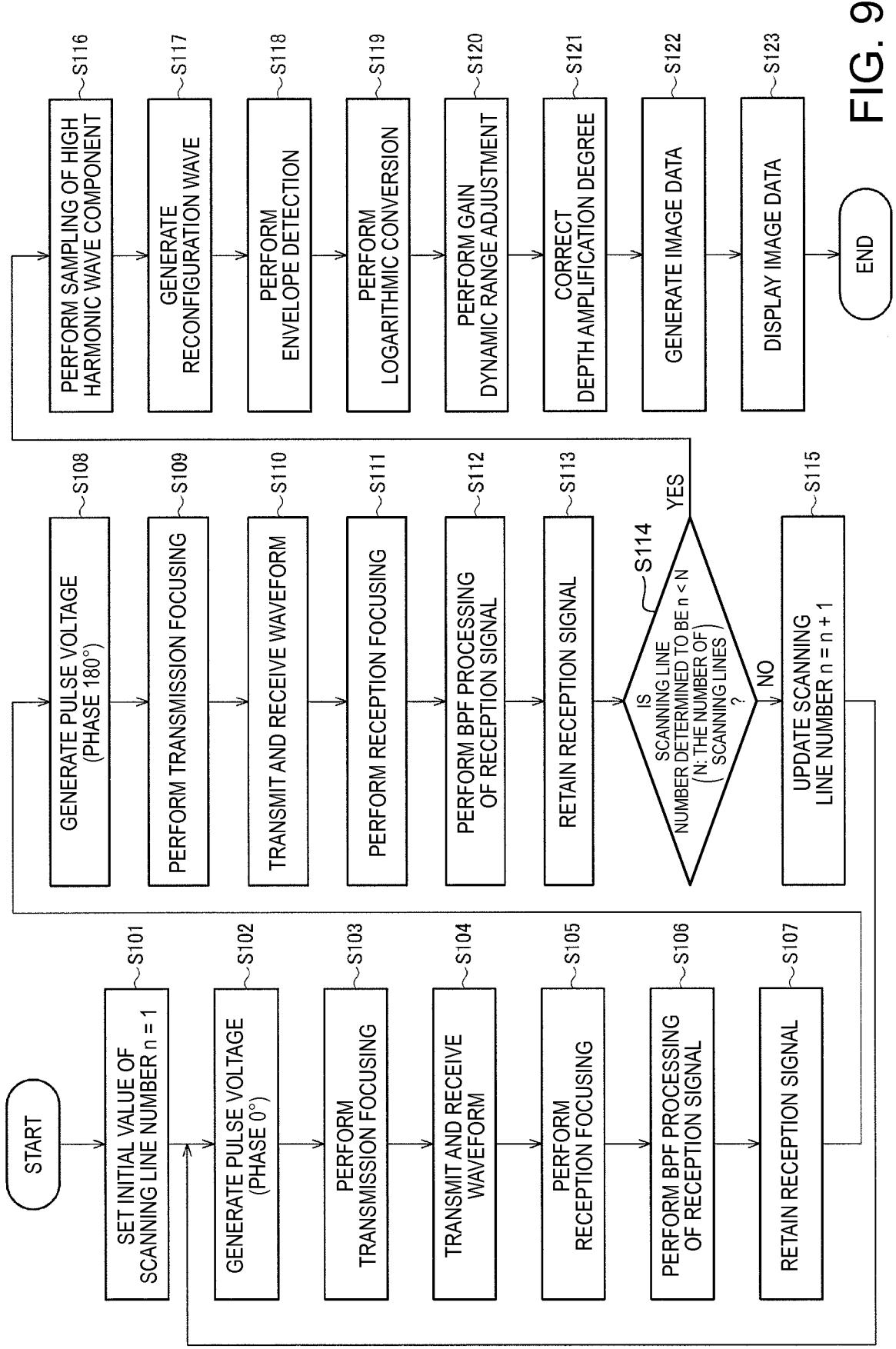
FIG. 9 is a flow chart illustrating a flow of overall processing of the embodiment.
Figure 10:
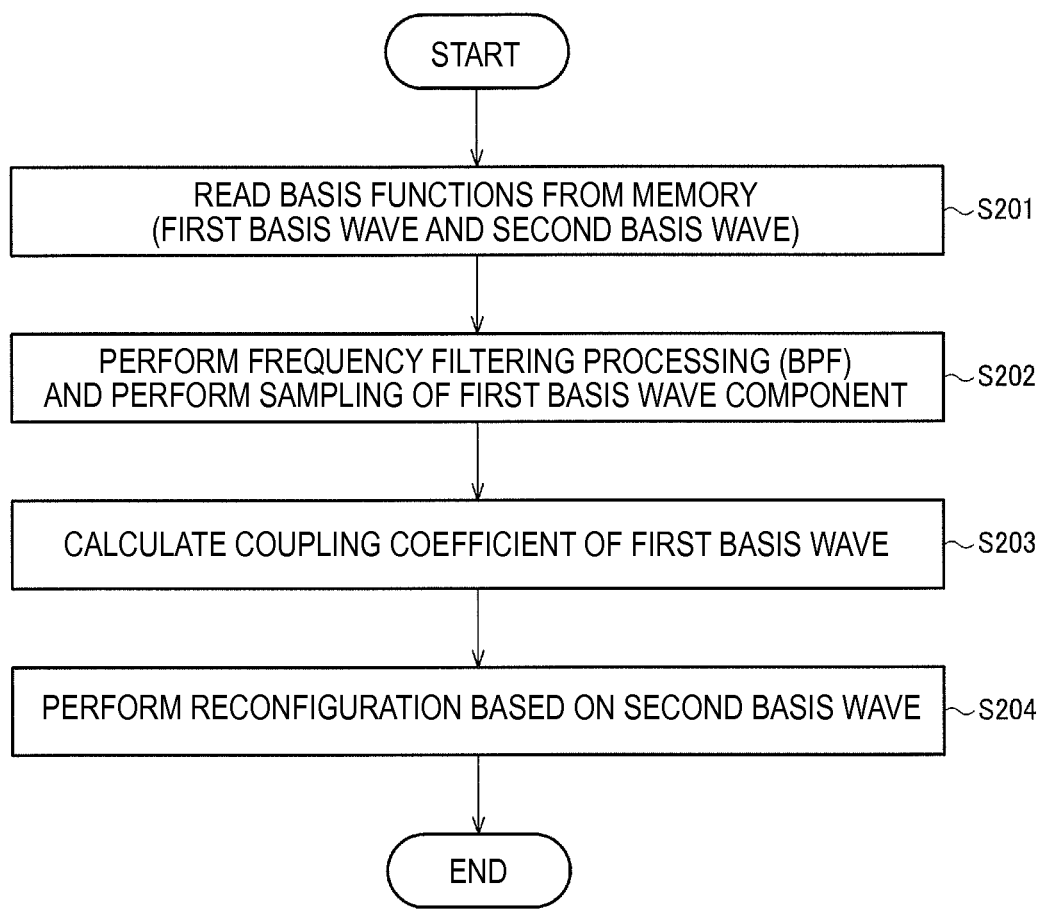
FIG. 10 is a flow chart illustrating a flow of the generation processing of the reconfiguration wave.
Figure 11:
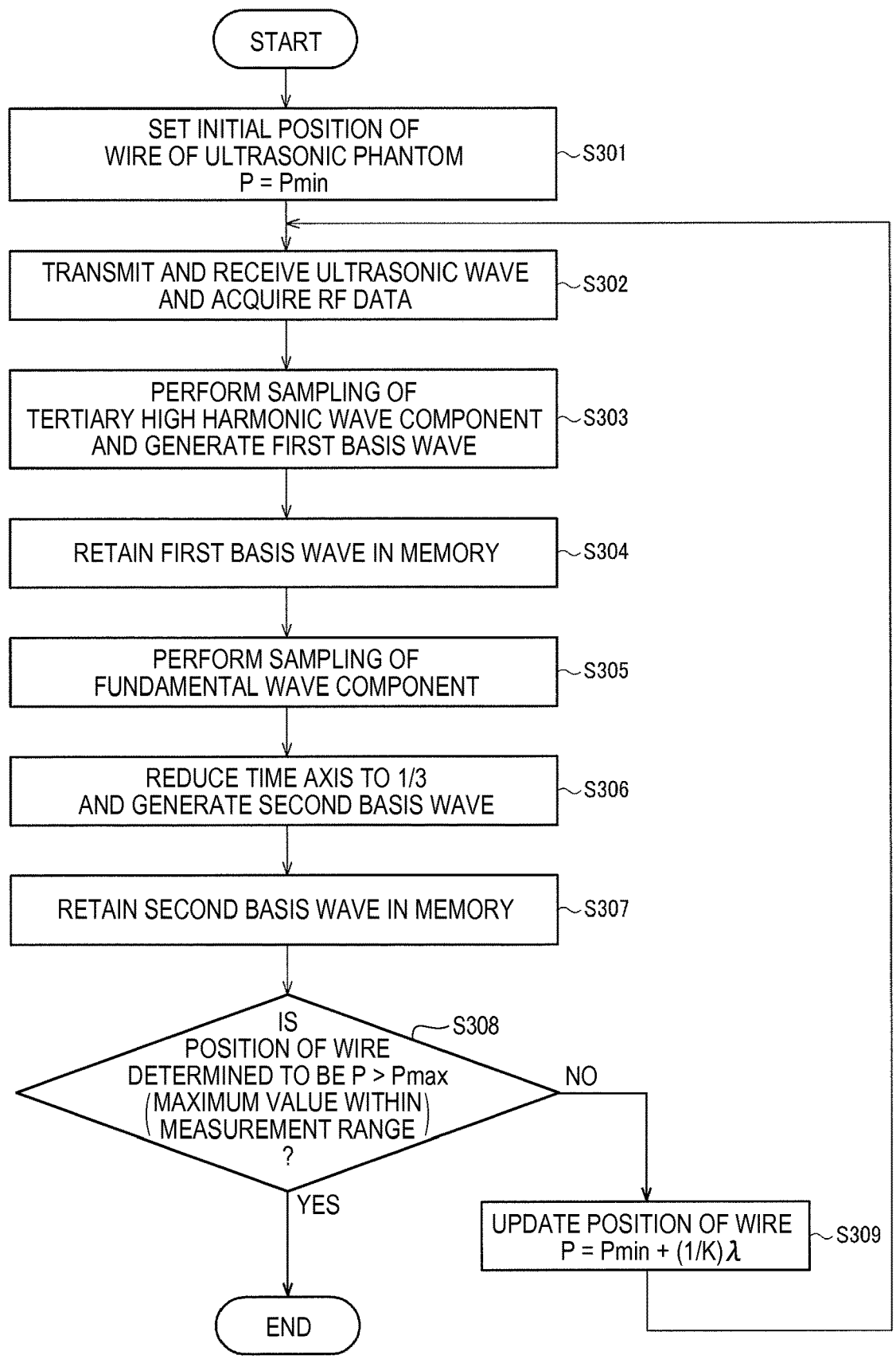
FIG. 11 is a flow chart illustrating a flow of the generation processing of a first basis wave and a second basis wave.

The first basis wave and the second basis wave used in the processing in the flow chart of FIGS. 9 and 10 need to be generated and to be stored in the memory (not illustrated) in advance before the steps of the processing are performed (preprocessing). Hereinafter, a flow of the generation processing of the first basis wave and the second basis wave will be described with reference to the flow chart of FIG. 11.

First, an initial position P of a wire of an ultrasonic phantom is set (S301). In this case, the initial position P is set to a position $P_{min}$ which is closest to the measurement surface of the ultrasonic probe in the ultrasonic measurement apparatus. The position of the wire denotes a position of the point scatterer.

The transmission processing unit 110 transmits two pulse signals having phases mutually inverted to the target object (the ultrasonic phantom), and the reception processing unit 120 receives each of the two reception signals (RF data) respectively corresponding to the two transmitted pulse signals (S302).

As described in FIGS. 2B and 2C, the processing unit 130 performs the subtraction processing based on the two reception signals respectively corresponding to the two transmitted pulse signals, thereby obtaining one differential signal. As described in FIGS. 3A and 3B, the first filtering processing is performed with respect to the obtained differential signal, thereby sampling the high harmonic wave component (the tertiary high harmonic wave component). Here, the first filtering processing denotes the high-pass filtering processing or the band-pass filtering processing, for example.

Moreover, the processing unit 130 obtains the high harmonic wave corresponding to the reflected wave component from the point scatterer which is arranged at the given measurement point based on the sampled high harmonic wave component, as the first basis wave (S303).

In the examples of FIGS. 8A and 8B described above, the reception wave (the high harmonic wave) X includes the reflected wave components from the various point scatterers inside the target object. Therefore, unless the comparison is performed with respect to the first basis wave which is specified in advance, it is not possible to specify the first basis wave component from the given measurement point which is included in the reception wave X. In contrast, in the processing, the high harmonic wave component after being subjected to the first filtering processing includes only the reflected wave component from the point scatterer which is arranged at the given measurement point inside the ultrasonic phantom. Even though the high harmonic wave component includes noise and the like, it is possible to be easily isolated from the noise component.

Therefore, it is possible to specify the first basis wave corresponding to the reflected wave component from the point scatterer at the given measurement point inside the target object. The processing unit 130 retains the specified first basis wave in the memory (S304).

Figure 12A:
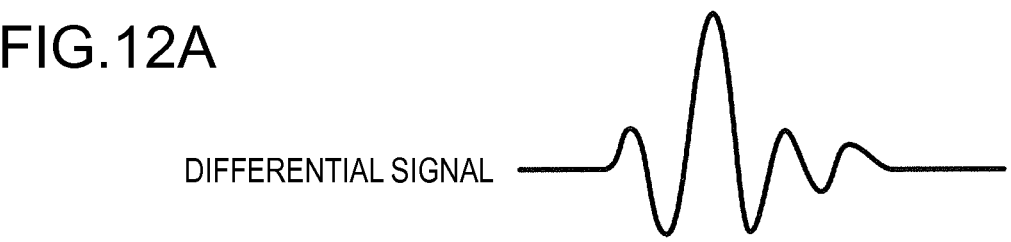
FIGS. 12A to 12C are detailed explanatory diagrams of the generation processing of the second basis wave.
Figure 12B:
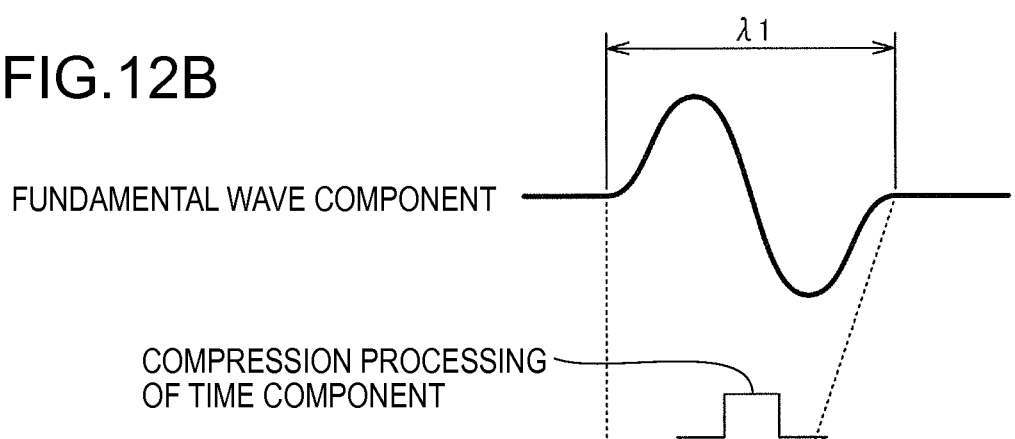
Figure 12C:
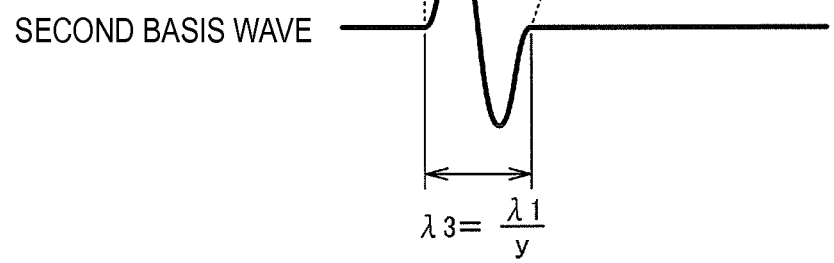

Moreover, the processing unit 130 performs the second filtering processing with respect to the differential signal which is obtained through the subtraction processing illustrated in FIG. 12A, thereby sampling the fundamental wave component as illustrated in FIG. 12B (S305). The processing unit 130 obtains the fundamental wave corresponding to the reflected wave component from the point scatterer which is arranged at the given measurement point based on the sampled fundamental wave component. The processing unit 130 performs the compression processing of the time component with respect to the obtained fundamental wave as illustrated in FIG. 12C, thereby obtaining the second basis wave (S306). When processing of compressing the time component to 1/y is performed, the wavelength λ3 of the second basis wave in FIG. 12C becomes 1/y (y is a positive number) of the wavelength λ1 of the fundamental wave in FIG. 12B.

In this manner, it is possible to specify the second basis wave which is obtained by shortening the wavelength of the first basis wave corresponding to the reflected wave component from the point scatterer at the given measurement point inside the target object.

The second basis wave can be obtained by performing the compression processing of the time component with respect to the fundamental wave which can be sampled from the reception signal.

Accordingly, it is possible to specify the second basis wave through simple steps of processing such as the subtraction processing, the filtering processing, and the compression processing of the time component. The processing unit 130 retains the specified second basis wave in the memory (S307).

Thereafter, the processing unit 130 determines whether or not the position P of the wire is greater than the maximum value $P_{max}$ within the measurement range (S308), and when it is determined that the position P of the wire is equal to or less than the maximum value $P_{max}$ within the measurement range, the position P of the wire is updated based on the following Expression 4 (S309), thereby returning to Step S302. In Expression 4, the factor K is a given constant, and the factor λ is a wavelength.

$$P=P_{min}+(1/K)\lambda \qquad (4)$$

Meanwhile, when it is determined that the position P of the wire is greater than the maximum value $P_{max}$ within the measurement range, the processing unit 130 ends the processing.

In brief, as illustrated in FIGS. 13A and 13B for example, the ith first basis wave $s_i$ among the M first basis waves is the high harmonic wave corresponding to the reception signal of the ultrasonic wave from an ith point scatterer SPi which is arranged at the ith measurement point. The factor M is an integer equal to or greater than 2, and the factor i is an integer of 1≤i≤M.

Moreover, an (i+1)th first basis wave $s_{(i+1)}$ among the M first basis waves is the high harmonic wave corresponding to the reception signal of the ultrasonic wave from an (i+1)th point scatterer SP(i+1) arranged at the (i+1)th measurement point which is a position farther than the ith measurement point, from a transmission point TP of the ultrasonic wave.

Accordingly, it is possible to perform sampling of the first basis wave component from the reception wave with the distance resolution corresponding to the gap of each of the set measurement points.

For example, as illustrated in FIGS. 13A and 13C, a jth second basis wave $s'_j$ among the N second basis waves is the high harmonic wave corresponding to the reception signal of the ultrasonic wave from a jth point scatterer SPj which is arranged at the jth measurement point. The factor N is an integer equal to or greater than 2, and the factor j is an integer of 1≤j≤N. In the example, there is a relationship of M=N. However, there may be a relationship of M≠N.

Moreover, a (j+1)th second basis wave $s'_{(j+1)}$ among the N second basis waves is the high harmonic wave corresponding to the reception signal of the ultrasonic wave from the (j+1)th point scatterer SP(j+1) arranged at the (j+1)th measurement point which is the position farther than the jth measurement point, from the transmission point TP of the ultrasonic wave.

Accordingly, it is possible to improve the distance resolution in the measurement result of the target object obtained by using an ultrasonic wave to correspond to the gap between each of the set measurement points.

However, the generation processing of the first basis wave and the second basis wave of the embodiment is not limited to the processing described above. For example, each of the second basis waves may be generated by reducing the number of wave cycles of each of the corresponding first basis wave. Moreover, without performing the generation processing of the first basis wave and the second basis wave, the first basis wave and the second basis wave stored in the memory in advance may be used. The ultrasonic probe and the measurement point may be obtained through simulation.

3.3. Measurement Result

Figure 14A:
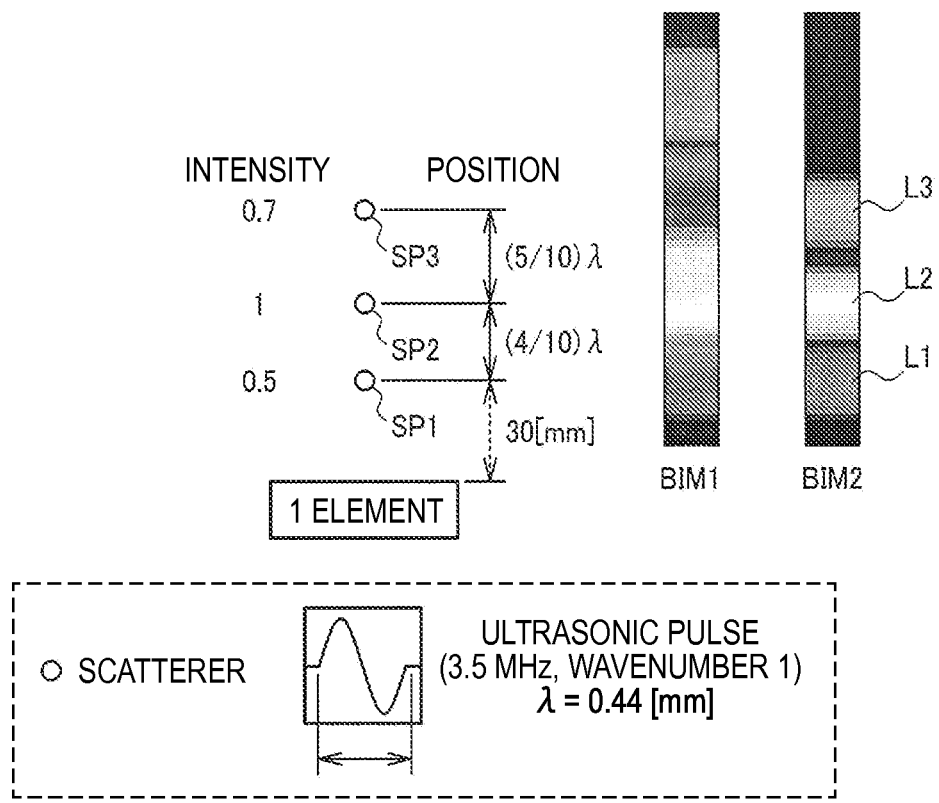
FIGS. 14A and 14B are explanatory diagrams of a measurement result.
Figure 14B:
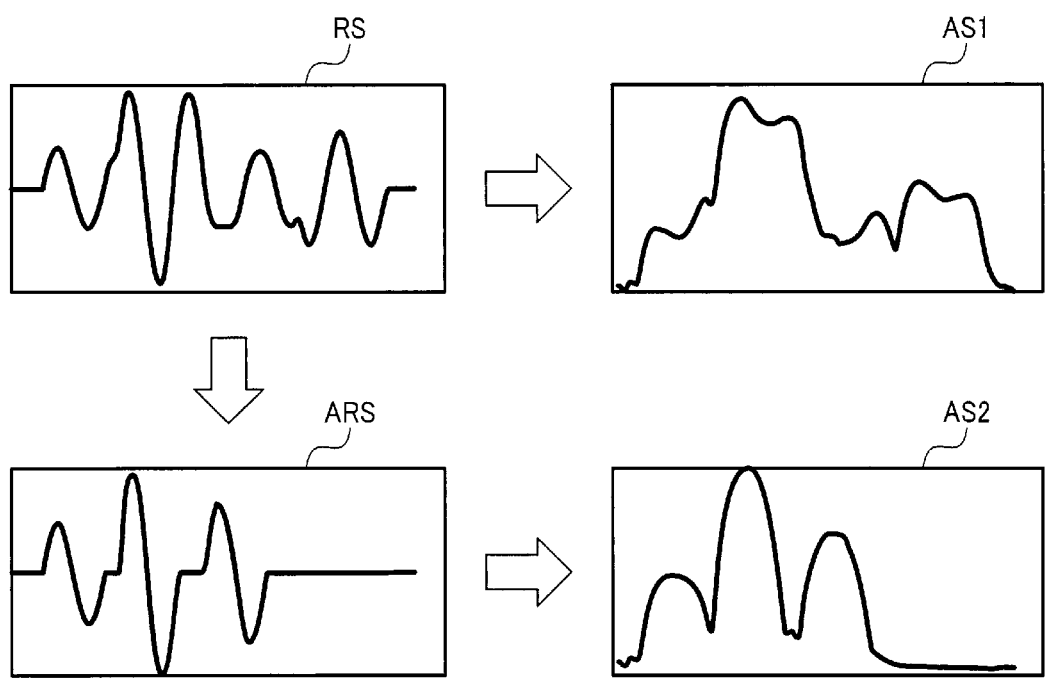

FIGS. 14A and 14B illustrate an example of the measurement result of the embodiment. In the example, as illustrated in FIG. 14A, the ultrasonic pulse transmitted to the target object is exemplified under the conditions of the wavelength $\lambda=0.44$ mm, the number of wave cycles of 1, and the frequency of 3.5 MHz.

In the example of FIG. 14A, it is considered that the upper direction of the diagram is the depth direction of the target object, and there exist three point scatterers (SP1 to SP3) inside the target object. It is considered that the ultrasonic transducer element and the point scatterer SP1 are separated from each other by 30 mm, the point scatterer SP1 and the point scatterer SP2 are separated from each other by $(4/10)\lambda$, and the point scatterer SP2 and the point scatterer SP3 are separated from each other by $(5/10)\lambda$. Moreover, it is considered that the reflection intensity from the point scatterer SP1 is 0.5, the reflection intensity from the point scatterer SP2 is 1.0, and the reflection intensity from the point scatterer SP3 is 0.7.

In this case, when a B-mode image is generated by using only the phase inversion method and the filtering method, an image BIM1 shown in FIG. 14A is generated. In the image BIM1, since the reflected waves from each of the point scatterers overlap with one another, the overall tone of the image is unlikely to vary, and thus, it is difficult to specify the positions of three point scatterers in detail.

Meanwhile, when a B-mode image is generated based on the reconfiguration wave according to the above-described embodiment, an image BIM2 shown in FIG. 14A is generated. As is clear in the image BIM2, a color layer L1 corresponds to the reflection from a point scatterer SP1, a color layer L2 corresponds to the reflection from a point scatterer SP2, and a color layer L3 corresponds to the reflection from a point scatterer SP3. In other words, the distance resolution is improved compared to the technique using only the phase inversion method and the filtering method.

The processing unit 130 may perform the envelope detection processing with respect to the reconfiguration signal which is obtained after being subjected to the conversion processing.

For example, as illustrated in FIG. 14B, when the envelope detection processing is performed with respect to the waveform after the processing using the phase inversion method and the filtering method is performed with respect to the reception signal RS, a waveform AS1 can be obtained. In the waveform AS1, two significant mountainous curves can be checked. However, it is difficult to determine that three point scatterers are included in the target object, based on the mountainous curves.

In contrast, as the processing of the embodiment is performed with respect to the reception signal RS, the waveform ARS is obtained, and as the envelope detection processing is performed with respect to the waveform ARS, a waveform AS2 can be obtained. In the waveform AS2, three mountainous curves can be checked, and it is possible to easily determine that the mountainous curves are the curves corresponding to the reflection from the point scatterers. The positions of the mountainous curves in the waveform AS2 exhibit a state closer to the distribution of the point scatterers in the actual target object, compared to the waveform AS1.

In this manner, it is possible to cause the display unit 300 to display the waveform data so that a user can easily discriminate the measurement result.

4. Ultrasonic Transducer Element

Figure 15A:
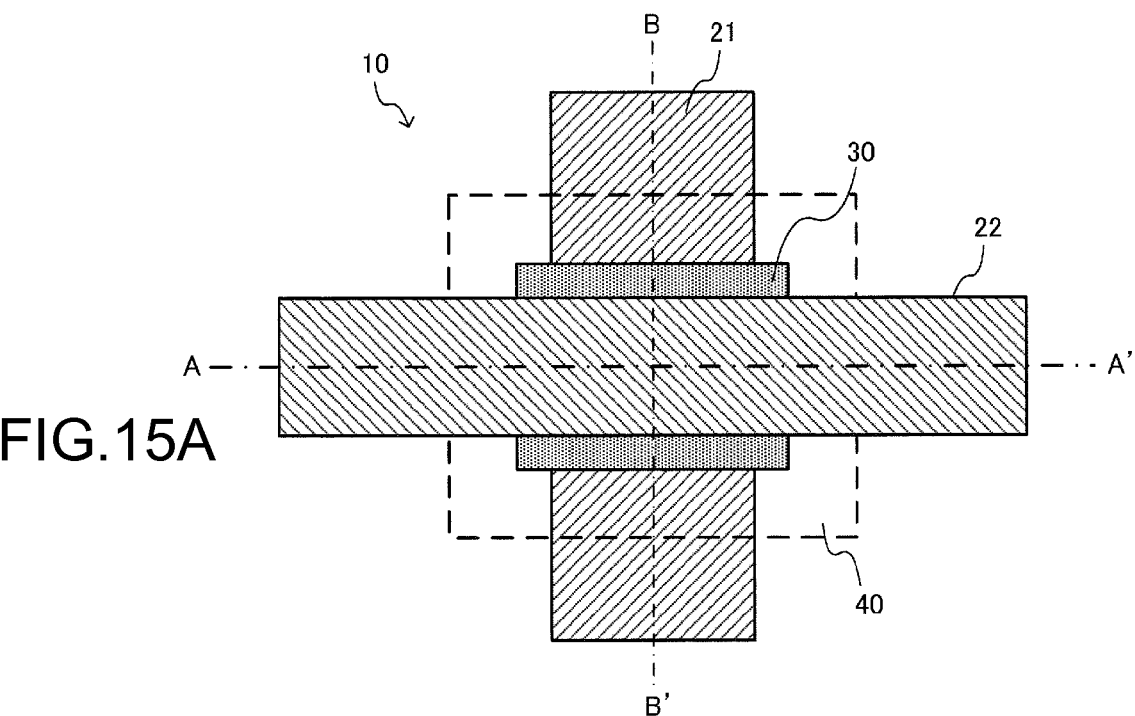
FIGS. 15A to 15C are configuration examples of an ultrasonic transducer element.
Figure 15B:
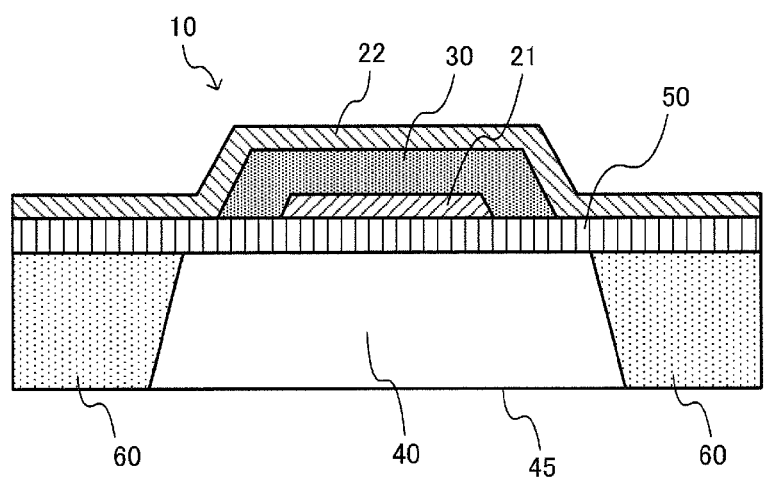
Figure 15C:
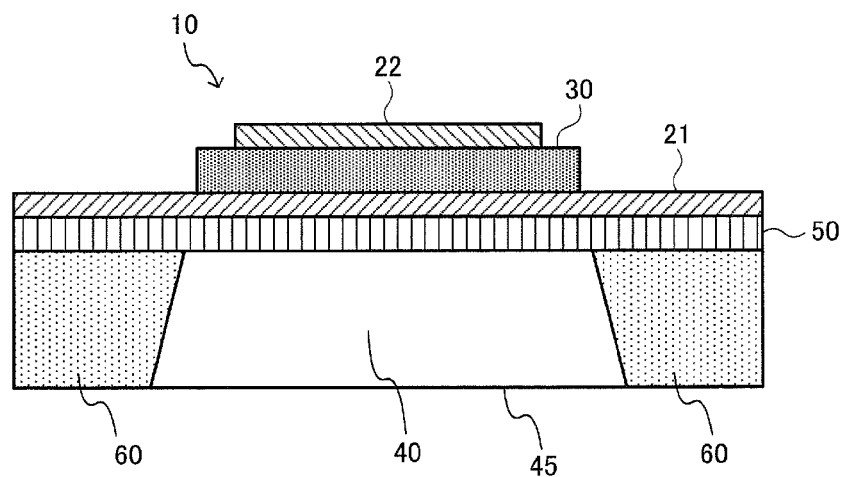

FIGS. 15A to 15C illustrate a configuration example of an ultrasonic transducer element 10 of the ultrasonic transducer device. The ultrasonic transducer element 10 includes a vibration film (a membrane and a support member) 50 and a piezoelectric element portion. The piezoelectric element portion includes a first electrode layer (a lower electrode) 21, a piezoelectric layer (a piezoelectric film) 30, and a second electrode layer (an upper electrode) 22.

FIG. 15A is a plan view of the ultrasonic transducer element 10 which is formed in a substrate (a silicon substrate) 60 seen in a direction vertical to the substrate 60 on the element forming surface side. FIG. 15B is a cross-sectional view illustrating a cross section taken along line A-A' in FIG. 15A. FIG. 15C is a cross-sectional view illustrating a cross section taken along line B-B' in FIG. 15A.

The first electrode layer 21 is formed with a metallic thin film, for example, on an upper layer of the vibration film 50. The first electrode layer 21 may be a wire which extends to the outside of an element forming region as illustrated in FIG. 15A and is connected to the adjacent ultrasonic transducer element 10.

For example, the piezoelectric layer 30 is formed with a lead zirconate titanate (PZT) thin film and is provided so as to cover at least a portion of the first electrode layer 21. The material of the piezoelectric layer 30 is not limited to PZT. For example, lead titanate (PbTiO3), lead zirconate (PbZrO3), titanate lead lanthanum ((Pb, La)TiO3), and the like may be used.

For example, the second electrode layer 22 is formed with a metallic thin film and is provided so as to cover at least a portion of the piezoelectric layer 30. The second electrode layer 22 may be a wire which extends to the outside of an element forming region as illustrated in FIG. 15A and is connected to the adjacent ultrasonic transducer element 10.

For example, the vibration film (the membrane) 50 is provided so as to block an aperture 40 with a two-layer structure of a SiO2 thin film and a ZrO2 thin film. The vibration film 50 supports the piezoelectric layer 30, and first and second electrode layers 21 and 22. The vibration film 50 vibrates in accordance with expansion and contraction of the piezoelectric layer 30 and can generate ultrasonic waves.

The aperture 40 is formed by performing etching such as reactive ion etching (RIE) from a rear surface (a surface with no element formed thereon) side of the substrate 60 (the silicon substrate). The resonance frequency of the ultrasonic wave is decided in accordance with the size of an aperture portion 45 of the aperture 40, and the ultrasonic wave is emitted to the piezoelectric layer 30 side (in the front direction from the back on the sheet surface in FIG. 15A).

The lower electrode (a first electrode) of the ultrasonic transducer element 10 is formed by the first electrode layer 21, and the upper electrode (a second electrode) is formed by the second electrode layer 22. Specifically, a portion of the first electrode layer 21 covered with the piezoelectric layer 30 forms the lower electrode, and a portion of the second electrode layer 22 covering the piezoelectric layer 30 forms the upper electrode. In other words, the piezoelectric layer 30 is provided so as to be interposed between the lower electrode and the upper electrode.

5. Ultrasonic Transducer Device

Figure 16:
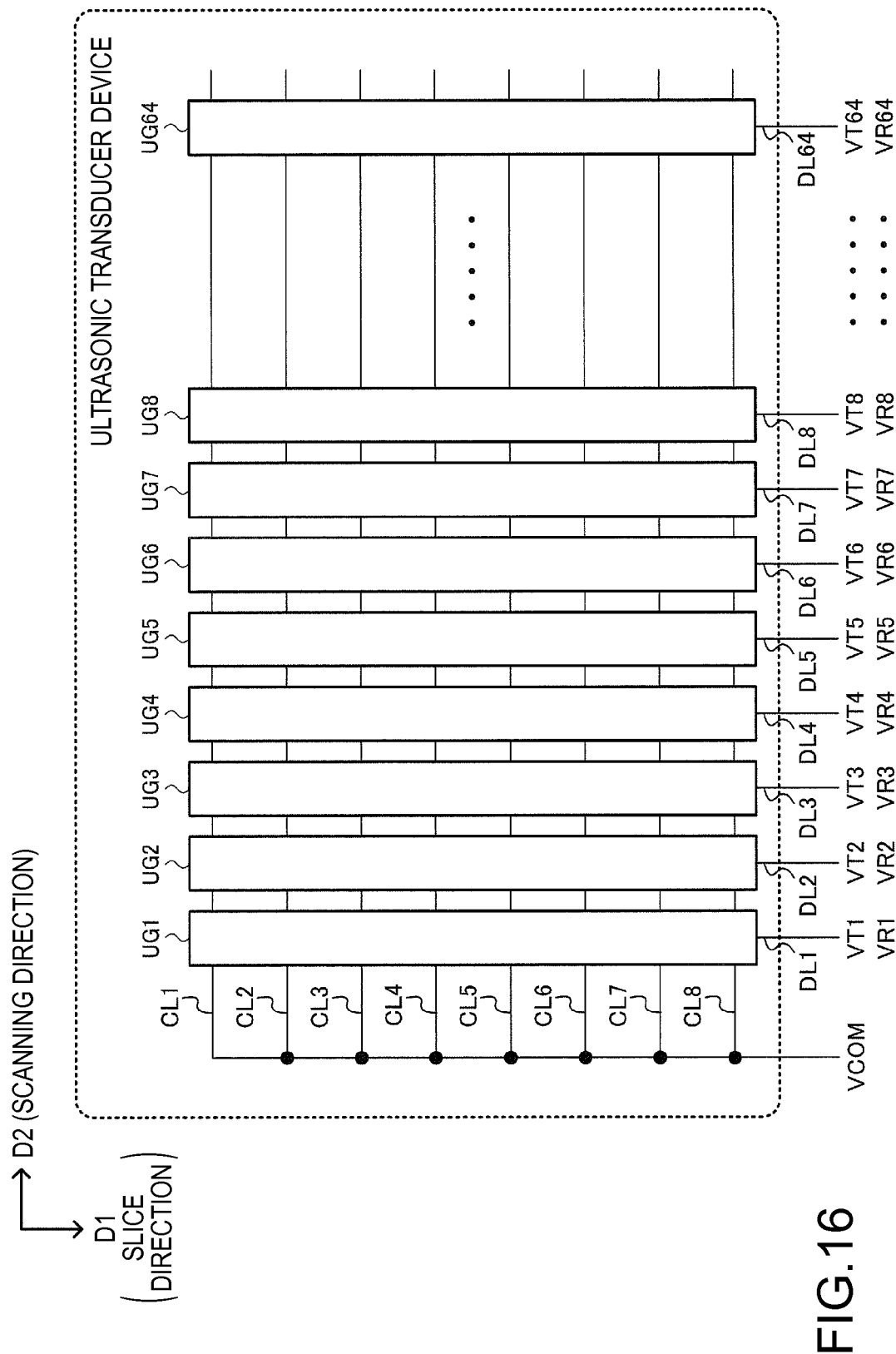
FIG. 16 is a configuration example of an ultrasonic transducer device.

FIG. 16 illustrates a configuration example of the ultrasonic transducer device (an element chip). The ultrasonic transducer device in this configuration example includes the plurality of ultrasonic transducer element groups UG1 to UG64, drive electrode lines DL1 to DL64 (in a broad sense, first to nth drive electrode lines. The factor n is an integer equal to or greater than 2), and common electrode lines CL1 to CL8 (in a broad sense, the first to mth common electrode lines. The factor m is an integer equal to or greater than 2). The number (n) of the drive electrode lines and the number (m) of the common electrode lines are not limited to the numbers illustrated in FIG. 16.

The plurality of ultrasonic transducer element groups UG1 to UG64 are arranged in 64 columns along a second direction D2 (a scan direction). Each of the ultrasonic transducer element groups UG1 to UG64 has the plurality of ultrasonic transducer elements which are arranged along a first direction D1 (a slice direction).

Figure 17A:
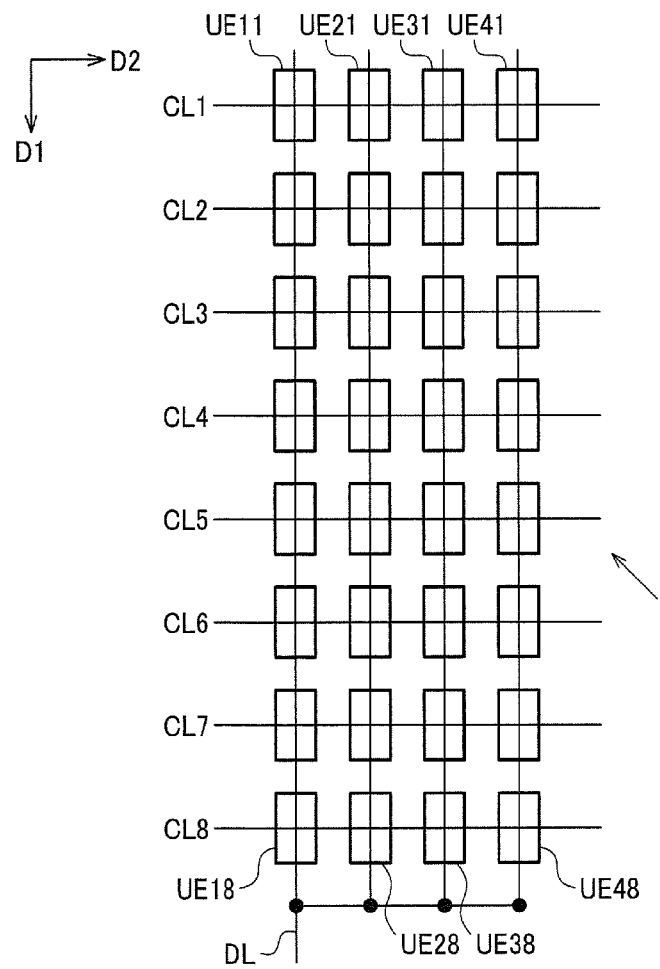
FIGS. 17A and 17B are configuration examples of an ultrasonic transducer element group each of which is provided while being corresponding to each of channels.

FIG. 17A illustrates an example of the ultrasonic transducer element group UG (UG1 to UG64). In FIG. 17A, the ultrasonic transducer element group UG is configured to have first to fourth element columns. The first element column is configured to have ultrasonic transducer elements UE11 to UE18 which are arranged along the first direction D1, and the second element column is configured to have ultrasonic transducer elements UE21 to UE28 which are arranged along the first direction D1. The third element column (UE31 to UE38) and the fourth element column (UE41 to UE48) are similar thereto as well. The drive electrode lines DL (DL1 to DL64) are commonly connected to the first to fourth element columns, and the common electrode lines CL1 to CL8 are connected to the ultrasonic transducer elements of the first to fourth element columns.

Figure 17B:
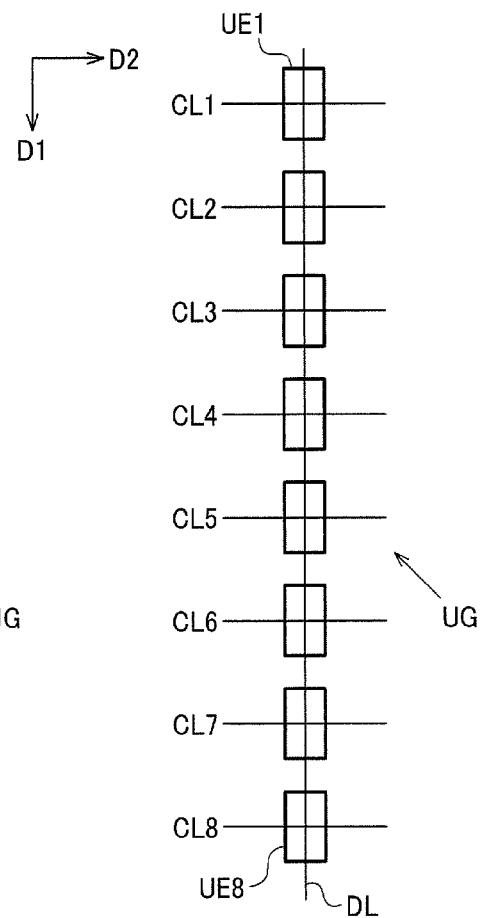

The ultrasonic transducer element group UG in FIG. 17A is configured to be one channel of the ultrasonic transducer device. In other words, the drive electrode line DL corresponds to the drive electrode line in one channel and a transmission signal of one channel from a transmission circuit is input to the drive electrode line DL. The reception signal of one channel from the drive electrode line DL is output from the drive electrode line DL. The number of element columns configuring one channel is not limited to four as described in FIG. 17A. The column may be fewer than four columns or more than four columns. For example, as illustrated in FIG. 17B, the number of the element columns may be one.

As illustrated in FIG. 16, the drive electrode lines DL1 to DL64 (the first to nth drive electrode lines) are wired along the first direction D1. A jth (j is an integer of 1≤j≤n) drive electrode line DLj (a jth channel) among the drive electrode lines DL1 to DL64 is connected to the first electrode (for example, the lower electrode) included in the ultrasonic transducer element of a jth ultrasonic transducer element group UGj.

During a transmission period in which ultrasonic waves are emitted, transmission signals VT1 to VT64 are supplied to the ultrasonic transducer element via the drive electrode lines DL1 to DL64. During a reception period in which ultrasonic echo signals are received, reception signals VR1 to VR64 are output from the ultrasonic transducer element to the drive electrode lines DL1 to DL64.

The common electrode lines CL1 to CL8 (the first to mth common electrode lines) are wired along the second direction D2. The second electrode included in the ultrasonic transducer element is connected to any one among the common electrode lines CL1 to CL8. Specifically, for example, as illustrated in FIG. 16, an ith (i is an integer of 1≤i≤m) common electrode line CLi among the common electrode lines CL1 to CL8 is connected to the second electrode (for example, the upper electrode) included in the ultrasonic transducer element which is arranged in an ith row.

A common voltage VCOM is supplied to the common electrode lines CL1 to CL8. The common voltage VCOM may be a constant direct current voltage and is not need to be 0V, that is, ground potential.

During the transmission period, a differential voltage between the transmission signal voltage and the common voltage is applied to the ultrasonic transducer element, and the ultrasonic wave at a predetermined frequency is emitted.

The arrangement of the ultrasonic transducer elements is not limited to the matrix arrangement illustrated in FIG. 16 and may be a so-called zig-zag arrangement or the like.

FIGS. 17A and 17B illustrate cases where one ultrasonic transducer element serves as both a transmission element and a reception element. However, the embodiment is not limited thereto. For example, the ultrasonic transducer element for a transmission element and the ultrasonic transducer element for a reception element may be separately provided in an array shape.

In the ultrasonic measurement apparatus, the ultrasonic imaging apparatus, and the like according to the embodiment, a portion or the majority of the processing may be realized by a program. In this case, as a processor such as a CPU executes a program, the ultrasonic measurement apparatus, the ultrasonic imaging apparatus, and the like according to the embodiment are realized. Specifically, a program stored in a non-temporary information storage device is read out, and the read out program is executed by the processor such as a CPU. Here, the information storage device (a computer readable device) stores a program, data, and the like. The function thereof can be realized by an optical disk (DVD, CD, and the like), a hard disk drive (HDD), a memory (a card-type memory, ROM, and the like), and the like. The processor such as a CPU performs various types of processing of the embodiment based on the program (data) stored in the information storage device. In other words, the information storage device stores a program for causing a computer (the apparatus including an operation unit, a processing unit, a storage unit, an output unit) to function as each unit of the embodiment (a program for causing a computer to execute the processing of each unit).

The ultrasonic measurement apparatus, the ultrasonic imaging apparatus, and the like according to the embodiment may include a processor and a memory. In this case, the processor may be a central processing unit (CPU), for example. However, the processor is not limited to the CPU, and various processors such as a graphics processing unit (GPU) and a digital signal processor (DSP) can be applied thereto. The processor may be a hardware circuit configured to be an application specific integrated circuit (ASIC). The memory stores commands readable by a computer. As the commands are executed by the processor, each unit of the ultrasonic measurement apparatus, the ultrasonic imaging apparatus, and the like according to the embodiment is realized. In this case, the memory may be semiconductor memory such as a static random access memory (SRAM) and a dynamic random access memory (DRAM), or may be a register, a hard disk, or the like. In this case, the commands may be a set of commands configuring a program, or may be commands for issuing instructions of manipulation with respect to the hardware circuit of the processor.

Hereinbefore, the embodiment is described in detail. However, it is possible for those skilled in the art to easily understand that new additions and various modifications without substantially departing from the invention can be made. Therefore, all the modification examples are considered to be included in the scope of the invention. For example, a term which has been disclosed at least once together with alternative term used in a wider sense or similar sense in this Specification and the drawings can be replaced with the alternative term at any place in this Specification and the drawings. The configurations and operations of the ultrasonic measurement apparatus, the ultrasonic imaging apparatus, and the ultrasonic measurement method are not also limited to those described in the embodiment. Therefore, various modifications can be executed.

The entire disclosure of Japanese Patent Application No. 2014-222474 filed on Oct. 31, 2014 is expressly incorporated by reference herein.

What is claimed is:

1. An ultrasonic measurement apparatus comprising:
a transmission processing unit that performs processing for transmitting an ultrasonic wave including a first ultrasonic wave in response to a transmission pulse signal including a first transmission pulse signal;
a reception processing unit that performs reception processing of an ultrasonic echo with respect to the transmitted ultrasonic wave so as to output a reception signal including a first reception signal; and
one or more processors programmed to:
specify coupling coefficients of respective first basis waves to configure the first reception signal, each of the first basis waves having a first number of wave cycles; and
perform conversion processing for converting the first reception signal into a reconfiguration signal, by representing the first reception signal as a sum of products, each product being formed between one of the specified coupling coefficients and corresponding one of second basis waves, the corresponding one of the second basis waves having a same phase difference as one of the first basis waves corresponding to the one of the specified coupling coefficients, each of the second basis waves having a second number of wave cycles that is less than the first number of wave cycles,
wherein each of the first basis waves and each of the second basis waves are obtained in response to a corresponding tertiary harmonic wave of a second reception signal that is reflected from a scatterer arranged at a corresponding depth in an ultrasonic phantom, and the second reception signal is generated in response to a second transmission pulse signal corresponding to a second ultrasonic wave that is transmitted to the scatterer arranged at the corresponding depth in the ultrasonic phantom.

2. The ultrasonic measurement apparatus according to claim 1,
wherein the one or more processors are programmed to perform the conversion processing after the specifying of the coupling coefficients of the first basis waves with respect to the tertiary harmonic wave corresponding to the first reception signal so as to generate a reconfiguration wave obtained by the second basis waves as the reconfiguration signal.

3. An ultrasonic imaging apparatus comprising:
the ultrasonic measurement apparatus according to claim 2; and
a display unit that displays image data generated based on the reconfiguration signal.

4. The ultrasonic measurement apparatus according to claim 1,
wherein the first basis waves amount to M (M is an integer equal to or greater than 2) first basis waves, wherein an ith (i is an integer of 1 i M) first basis wave among the M first basis waves is the tertiary harmonic wave corresponding to the second reception signal of the second ultrasonic wave from an ith point scatterer which is arranged at an ith measurement point, and
wherein an (i+1)th first basis wave among the M first basis waves is the tertiary harmonic wave corresponding to the second reception signal of the second ultrasonic wave from an (i+1)th point scatterer which is arranged at an (i+1)th measurement point at a position farther than the ith measurement point from a transmission point of the second ultrasonic wave.

5. An ultrasonic imaging apparatus comprising:
the ultrasonic measurement apparatus according to claim 4; and
a display unit that displays image data generated based on the reconfiguration signal.

6. The ultrasonic measurement apparatus according to claim 1,
wherein each of the first basis waves is the tertiary harmonic wave which is obtained by sampling the second reception signal.

7. An ultrasonic imaging apparatus comprising:
the ultrasonic measurement apparatus according to claim 6; and
a display unit that displays image data generated based on the reconfiguration signal.

8. The ultrasonic measurement apparatus according to claim 1,
wherein the transmission processing unit transmits two pulse signals having phases mutually inverted as the transmission pulse signal, and
wherein the one or more processors are programmed to:
perform subtraction processing based on the two second reception signals corresponding to the second transmission pulse signals to obtain one differential signal;
perform first filtering processing with respect to the obtained differential signal; and
perform sampling of a harmonic wave component to obtain the tertiary harmonic wave as first basis waves corresponding to a reflected wave component from the scatterer which is arranged at the corresponding depth in the ultrasonic phantom based on the sampled harmonic wave component.

9. An ultrasonic imaging apparatus comprising:
the ultrasonic measurement apparatus according to claim 8; and
a display unit that displays image data generated based on the reconfiguration signal.

10. The ultrasonic measurement apparatus according to claim 1,
wherein the first basis waves amount to M (M is an integer equal to or greater than 2) first basis waves,
wherein an ith (i is an integer of 1 i M) first basis wave among the M first basis waves and the (i+1)th first basis wave are shifted from each other in phase by a phase difference shorter than the phase difference corresponding to a pulse width of the second transmission pulse signal or a pulse width of the second reception signal.

11. An ultrasonic imaging apparatus comprising:
the ultrasonic measurement apparatus according to claim 10; and
a display unit that displays image data for displaying generated based on a reconfiguration signal.

12. The ultrasonic measurement apparatus according to claim 1,
wherein the second basis waves amount to N (N is an integer equal to or greater than 2) second basis waves,
wherein a jth (j is an integer of 1 j N) second basis wave among the N second basis waves is the tertiary harmonic wave corresponding to the second reception signal of the second ultrasonic wave from a jth point scatterer which is arranged at a jth measurement point, and
wherein a (j+1)th second basis wave among the N second basis waves is the tertiary harmonic wave corresponding to the second reception signal of the second ultrasonic wave from a (j+1)th point scatterer which is arranged at a (j+1)th measurement point at a position farther than the jth measurement point from a transmission point of the second ultrasonic wave.

13. The ultrasonic measurement apparatus according to claim 1,
wherein the second basis waves are obtained by performing compression processing of a time component with respect to a fundamental wave which is sampled from the second reception signal.

14. The ultrasonic measurement apparatus according to claim 1,
wherein the transmission processing unit transmits two pulse signals having phases mutually inverted, and
wherein the one or more processors performs subtraction processing based on the two second reception signals corresponding to the two second transmission pulse signals, obtains one differential signal, performs second filtering processing with respect to the obtained differential signal, performs sampling of a fundamental wave component, obtain a fundamental wave corresponding to a reflected wave component from a point scatterer which is arranged at a given measurement point, based on the sampled fundamental wave component, performs compression processing of a time component with respect to the obtained fundamental wave, and obtains the second basis wave.

15. The ultrasonic measurement apparatus according to claim 1,
wherein each of the second basis waves has a same phase difference as each of the first basis waves.

16. The ultrasonic measurement apparatus according to claim 1,
wherein the one or more processors are programmed to perform envelope detection processing with respect to the reconfiguration signal which is obtained in the conversion processing.

17. The ultrasonic measurement apparatus according to claim 1,
wherein the one or more processors perform deconvolution processing of the first reception signal as the coupling coefficient specification processing.

18. The ultrasonic measurement apparatus according to claim 1,
wherein the one or more processors perform convolution processing of the second basis wave as the conversion processing of the reconfiguration signal.

19. An ultrasonic imaging apparatus comprising:
the ultrasonic measurement apparatus according to claim 1; and
a display unit that displays image data generated based on the reconfiguration signal.

20. An ultrasonic measurement method comprising:
transmitting an ultrasonic wave including a first ultrasonic wave in response to a transmission pulse signal including a first transmission pulse signal;
receiving an ultrasonic echo with respect to the transmitted ultrasonic wave so as to output a reception signal including a first reception signal;
specifying coupling coefficients of respective first basis waves to configure the first reception signal, each of the first basis waves having a first number of wave cycles; and
converting the first reception signal into a reconfiguration signal, by representing the first reception signal as a sum of products, each product being formed between one of the specified coupling coefficients and corresponding one of second basis waves, the corresponding one of the second basis waves having a same phase difference as one of the first basis waves corresponding to the one of the specified coupling coefficients, each of the second basis waves having a second number of wave cycles that is less than the first number of wave cycles,
wherein each of the first basis waves and each of the second basis waves are obtained in response to a corresponding tertiary harmonic wave of a second reception signal that is reflected from a scatterer arranged at a corresponding depth in an ultrasonic phantom, and the second reception signal is generated in response to a second transmission pulse signal corresponding a second ultrasonic wave that is transmitted to the scatterer arranged at the corresponding depth in the ultrasonic phantom.

* * * * *